US012802824B2

United States Patent
(12) United States Patent
Mallozzi et al.

(10) Patent No.: US 12,802,824 B2
(45) Date of Patent: Nov. 17, 2026

(54) AUTOMATED SYSTEM AND METHODS TO EVALUATE PLANNED TREATMENT PERFORMANCE AND REAL TREATMENT PERFORMANCE USING THREE-DIMENSIONAL VIRTUAL DENTAL MODELS

(71) Applicant: Candid Care Co., New York, NY (US)

(72) Inventors: Thomas John Mallozzi, Saint Petersburg, FL (US); Anthony William Morefield, San Jose, CA (US); James A. Churchill, La Selva Beach, CA (US)

(73) Assignee: Candid Care Co., New York, NY (US)

( * ) Notice: Subject to any disclaimer, the term of this patent is extended or adjusted under 35 U.S.C. 154(b) by 41 days.

(21) Appl. No.: 18/626,587

(22) Filed: Apr. 4, 2024

(65) Prior Publication Data

US 2025/0316393 A1 Oct. 9, 2025

(51) Int. Cl.

*G16H 50/50* (2018.01)
*G06T 17/20* (2006.01)
*G16H 20/00* (2018.01)

(52) U.S. Cl.

CPC ........... *G16H 50/50* (2018.01); *G06T 17/205* (2013.01); *G16H 20/00* (2018.01); *G06T 2207/30036* (2013.01)

(58) Field of Classification Search

CPC ........ G16H 50/50; G16H 20/00; G16H 20/40; G16H 30/40; G06T 17/205;

(Continued)

(56) References Cited

U.S. PATENT DOCUMENTS

2005/0048432 A1* 3/2005 Choi ...................... A61C 7/002 433/24
2005/0271996 A1* 12/2005 Sporbert .................. A61C 7/00 433/24

(Continued)

OTHER PUBLICATIONS

OrthoCAD User Manual Version 5.9.1.50 (Year: 2022).*

(Continued)

*Primary Examiner* — Joshua B Blanchette
(74) *Attorney, Agent, or Firm* — Venable LLP

(57) ABSTRACT

The present disclosure provides a method of automatically determining orthodontic treatment plan scores and performance scores using three-dimensional (3D) virtual models. The associated computer implemented software system includes an input module configured to obtain, in a computer-implemented software system, at least one of virtual stage models or dental mesh models. Embodiments may also include a processing module configured to process the virtual stage models and/or the dental mesh models to generate one or more composite stage models. Additionally, a measurement module is configured to determine virtual measurement values from named objects within virtual stage models and/or composite stage models. Embodiments of the present disclosure may also include a module configured to apply index classifiers to determined virtual measurement values and calculate total performance scores and standardized performance scores. An output module is included to output, from the computer-implemented software system, planned treatment scores and treatment performance scores.

37 Claims, 28 Drawing Sheets

(58) Field of Classification Search
CPC ............. G06T 2207/30036; G06T 7/00; G06T 2210/41; G06T 17/00
USPC .......................................................... 705/2, 3
See application file for complete search history.

(56) References Cited

U.S. PATENT DOCUMENTS

| | | | | |
|---|---|---|---|---|
| 2008/0305454 | A1* | 12/2008 | Kitching | A61C 7/00 433/24 |
| 2020/0187851 | A1* | 6/2020 | Offenbacher | G16H 50/30 |
| 2022/0384046 | A1 | 12/2022 | Saliman et al. | |
| 2023/0129379 | A1* | 4/2023 | Li | A61C 7/002 382/128 |
| 2024/0261063 | A1* | 8/2024 | McGann | A61B 34/10 |

OTHER PUBLICATIONS

Buschang PH, Ross M, Shaw SG, Crosby D, Campbell PM. Predicted and actual end-of-treatment occlusion produced with aligner therapy. Angle Orthod. 2015;85(5):723 (Year: 2015).*

Alex Bulatkin, "Automate file retrieval from S3 Glacier when using FSx for Lustre"; Nov. 26, 2021 (Year: 2021).*

Dragstrem K, Galang-Boquiren MT, Obrez A, Costa Viana MG, Grubb JE, Kusnoto B. Accuracy of digital American Board of Orthodontics Discrepancy Index measurements. Am J Orthod Dentofacial Orthop. Jul. 2015;148(1):60-6. doi: 10.1016/j.ajodo.2015.02.027. PMID: 26124028. (Year: 2015).*

Scott JD, English JD, Cozad BE, Borders CL, Harris LM, Moon AL, Kasper FK. Comparison of automated grading of digital orthodontic models and hand grading of 3-dimensionally printed models. Am J Orthod Dentofacial Orthop. Jun. 2019;155(6):886-890. doi: 10.1016/j.ajodo.2018.11.011. PMID: 31153510. (Year: 2019).*

Horriat M, Bailey N, Atout B, Santos PB, Pinheiro FHSL. American Board of Orthodontics (ABO) Discrepancy Index and peer assessment rating (PAR) index with models versus photographs. J World Fed Orthod. Jun. 2022;11(3):83-89. doi: 10.1016/j.ejwf.2021.11.004. Epub Jan. 6, 2022. PMID: 34998719. (Year: 2022).*

International Search Report and Written Opinion for International Patent Application No. PCT/US2025/022992, dated Jul. 25, 2025.

* cited by examiner

Segmented Virtual Stage Model

Anatomical Object Labels

Anatomical Object Labels

| Tooth Object Labels | | | |
|---|---|---|---|
| Upper Right | Upper Left | Lower Right | Lower Left |
| UR1 | UL1 | LR1 | LL1 |
| UR2 | UL2 | LR2 | LL2 |
| UR3 | UL3 | LR3 | LL3 |
| UR4 | UL4 | LR4 | LL4 |
| UR5 | UL5 | LR5 | LL5 |
| UR6 | UL6 | LR6 | LL6 |
| UR7 | UL7 | LR7 | LL7 |
| UR8 | UL8 | LR8 | LL8 |

| Gingiva Object Labels | | | |
|---|---|---|---|
| Upper Right | Upper Left | Lower Right | Lower Left |
| gUR1 | gUL1 | gLR1 | gLL1 |
| gUR2 | gUL2 | gLR2 | gLL2 |
| gUR3 | gUL3 | gLR3 | gLL3 |
| gUR4 | gUL4 | gLR4 | gLL4 |
| gUR5 | gUL5 | gLR5 | gLL5 |
| gUR6 | gUL6 | gLR6 | gLL6 |
| gUR7 | gUL7 | gLR7 | gLL7 |
| gUR8 | gUL8 | gLR8 | gLL8 |

*FIG. 4b*

Virtual Dental Mesh Model

Composite Stage Model

Applied Measurements by ABO Index

| Discrepancy Index (DI) | Cast-Radiograph Evaluation (CR) |
|---|---|
| 1. Overjet (pre-treatment) | 1. Anterior Alignment |
| 2. Crowding | 2. Posterior Alignment |
| 3. Overbite | 3. Marginal Ridges |
| 4. Anterior Openbite | 4. Buccolingual Inclination |
| 5. Lateral Openbite | 5. Occlusal Contacts |
| 6. Lingual Posterior Crossbite | 6. Occlusal Relationship (post-treatment) |
| 7. Buccal Posterior Crossbite | 7. Posterior Overjet |
| 8. Occlusal Relationship (pre-treatment) | 8. Anterior Overjet |
| 9. Anomalous Morphology of Tooth Size | 9. Interproximal Contacts |
| 10. Midline Discrepancy | |
| 11. Generalized Spacing | |
| 12. Tooth Transposition | |

*FIG. 8*

(DI) Anterior Overjet (DI) Crowding (DI) Overbite (DI) Anterior Open Bite (DI) Lateral Open Bite (DI) Lingual Posterior Crossbite (DI) Buccal Posterior Crossbite (DI) Occlusal Relationship (DI) Anomalous Morphology (DI) Midline Discrepancy (DI) Spacing (DI) Tooth Transposition (CR) Alignment (CR) Marginal Ridges (CR) Buccolingual Inclination (CR) Anterior Overjet (CR) Posterior Overjet (CR) Occlusal Contacts (CR) Occlusal Relationship (CR) Interproximal Contact

(DI) Discrepancy Index Scorecard

EXAM YEAR ________ ABO DISCREPANCY INDEX

ABO ID # ________ CASE# _______ PATIENT ______________________________

TOTAL D.I. SCORE [ ]

*For mm measures, round up to the next full mm.*
*Examiners will verify measurements in each category.*

OVERJET

| | |
|---|---|
| ≥ 0 to < 1 mm (edge-to-edge) | = 1 pt |
| ≥ 1 to ≤ 3 mm | = 0 pts |
| > 3 to ≤ 5 mm | = 2 pts |
| > 5 to ≤ 7 mm | = 3 pts |
| > 7 to ≤ 9 mm | = 4 pts |
| > 9 mm | = 5 pts |
| Negative Overjet (x-bite): 1 pt per mm per tooth | = ____pts |
| Total | [ ] |

OVERBITE

| | |
|---|---|
| > 1 to ≤ 3 mm | = 0 pts |
| > 3 to ≤ 5 mm | = 2 pts |
| > 5 to ≤ 7 mm | = 3 pts |
| Impinging (100%) | = 5 pts |
| Total | [ ] |

ANTERIOR OPEN BITE

| | |
|---|---|
| 0 mm (edge-to-edge), 1 pt per tooth | = _____pts |
| then 1 pt per mm per tooth | = _____pts |
| Total | [ ] |

LATERAL OPEN BITE

| | |
|---|---|
| ≥ 0.5 mm, 2 pts per mm per tooth | |
| Total | [ ] |

CROWDING (only one arch)

| | |
|---|---|
| ≥ 0 to ≤1 mm | = 0 pts |
| > 1 to ≤ 3 mm | = 1 pts |
| > 3 to ≤ 5 mm | = 2 pts |
| > 5 to ≤ 7 mm | = 4 pts |
| > 7 mm | = 7 pts |
| Total | [ ] |

OCCLUSAL RELATIONSHIP

| | | |
|---|---|---|
| Class I to End On | = 0 pts | |
| End-to-End Class II or III | = 2 pts per side | _____pts |
| Full Class II or III | = 4 pts per side | _____pts |
| Beyond Class II or III | = 1 pt per mm additional | _____pts |
| Total | [ ] | |

30130315

LINGUAL POSTERIOR X-BITE

| | | |
|---|---|---|
| > 0 mm, 1 pt per tooth | Total | [ ] |

BUCCAL POSTERIOR X-BITE

| | | |
|---|---|---|
| > 0 mm, 2 pts per tooth | Total | [ ] |

CEPHALOMETRICS (See Instructions)

| | | |
|---|---|---|
| ANB ≥ 6° or ≤ -2° | @4pts | = ____ |
| Each full degree > 6° | ____x 1 pt | = ____ |
| Each full degree < -2° | ____x 1 pt | = ____ |
| SN-MP | | |
| ≥ 38° | @2pts | = ____ |
| Each full degree > 38° | ____x 2 pts | = ____ |
| ≤ 26° | @1pt | = ____ |
| Each full degree < 26° | ____x 1 pt | = ____ |
| $\bar{1}$ to MP ≥ 99° | @1pt | = ____ |
| Each full degree > 99° | ____x 1 pt | = ____ |
| | Total | [ ] |

OTHER (See Instructions)

| | | |
|---|---|---|
| Supernumerary teeth | ____x 1 pt | = ____ |
| Ankylosis of permanent teeth | ____x 2 pts | = ____ |
| Anomalous morphology | ____x 2 pts | = ____ |
| Impaction (except 3rd molars) | ____x 2 pts | = ____ |
| Midline discrepancy (≥3 mm) | @ 2 pts | = ____ |
| Missing teeth (except 3rd molars) | ____x 1 pt | = ____ |
| Missing teeth, congenital | ____x 2 pts | = ____ |
| Spacing (4 or more, per arch) | ____x 2 pts | = ____ |
| Spacing (mx cent diastema ≥ 2 mm) | @ 2 pts | = ____ |
| Tooth transposition | ____x 2 pts | = ____ |
| Skeletal asymmetry(nonsurgical tx) | @ 3 pts | = ____ |
| Addl. treatment complexities | ____x 2 pts | = ____ |

Identify:

[ ]

Total Other [ ]

*FIG. 29*

(CR) Cast-Radiograph Scoring

Reference - ABO Cast/Radiograph Evaluation

See Grading System for Casts-Radiographs for entire discussion

ALIGNMENT/ROTATIONS

0.5 – 1 mm = 1 for each tooth
> 1 mm = 2 for each tooth

OCCLUSAL CONTACTS

0 mm = satisfactory
≤ 1 mm = 1 (for each posterior
> 1 mm = 2 tooth out of contact)

Do not score diminutive distolingual cusps of the maxillary 1st and 2nd molars, nor lingual cusps of the mandibular first premolars. Maximum of 2 points per tooth**.

MARGINAL RIDGES

0.5 - 1 mm = 1 (for each interproximal contact
> 1 mm = 2 between posterior teeth)

Do not** include the canine-premolar contact.
Do not include the distal of lower 1st premolar.

OCCLUSAL RELATIONSHIP

< 1 mm = satisfactory
1 - 2 mm = 1 (for each maxillary tooth from the
> 2 mm = 2 the canines to the 2nd molars)

BUCCOLINGUAL INCLINATION

0 - 1 mm = satisfactory
1.1 - 2 mm = 1 ( for each posterior tooth)
> 2 mm = 2

Do not** score the mandibular 1st premolars nor the distal cusps of the second molars.

INTERPROXIMAL CONTACTS

0.6 - 1 mm = 1 (for each interproximal
> 1 mm = 2 contact)

OVERJET

Anterior teeth must be contacting.

0 mm = satisfactory
≤ 1 mm = 1 (for each maxillary
> 1 mm = 2 tooth)

Transverse posterior teeth:
Mandibular buccal cusps are measured to the central fossa of the maxillary teeth.

ROOT ANGULATION

Parallel = 0
Not parallel = 1
Root contacting adjacent root = 2 (for each occurrence )

Do not score the maxillary and mandibular canines.

NOTE: Gauge Width is 0.5 mm; Gauge Height is 1 mm
Third molars are not scored unless they substitute for the second molars.
No tooth is scored more than two points per individual parameter.

*FIG. 30a*

(CR) Cast-Radiograph Scorecard

Scores Output .JSON File Format

```
{
    "patientID": "9KUK6",
    "userName": "johndoe",
    "scores": [
        {
            "aboname": "OVERJET",
            "t1": 2,
            "t2": 0,
            "t3": 2
        },
        {
            "aboname": "CROWDING",
            "t1": 2,
            "t2": 0,
            "t3": 0
        },
        {
            "aboname": "OVERBITE",
            "t1": 3,
            "t2": 2,
            "t3": 2
        },
        {
            "aboname": "ANTERIOROPENBITE",
            "t1": 0,
            "t2": 0,
            "t3": 0
        },
        {
            "aboname": "LATERALOPENBITE",
            "t1": 2,
            "t2": 2,
            "t3": 16
        },
        {
            "aboname": "LINGUALPOSTERIORCROSSBITE",
            "t1": 0,
            "t2": 0,
            "t3": 1
        },
        {
            "aboname": "BUCCALPOSTERIORCROSSBITE",
            "t1": 2,
            "t2": 0,
            "t3": 0
        },
        {
            "aboname": "OCCLUSALRELATIONSHIPPRE",
            "t1": 0,
            "t2": 0,
            "t3": 2
        },
        {
            "aboname": "ANOMALOUSMORPHOLOGY",
            "t1": 0,
            "t2": 0,
            "t3": 0
        },
        {
            "aboname": "MIDLINEDISCREPANCY",
            "t1": 0,
            "t2": 0,
            "t3": 0
        },
        {
            "aboname": "GENERALIZEDSPACING",
            "t1": 0,
            "t2": 0,
            "t3": 0
        },
        {
            "aboname": "TOOTHTRANSPOSITION",
            "t1": 0,
            "t2": 0,
            "t3": 0
        },
        {
            "aboname": "ANTERIORALIGNMENT",
            "t1": 15,
            "t2": 3,
            "t3": 11
        },
        {
            "aboname": "POSTERIORALIGNMENT",
            "t1": 17,
            "t2": 11,
            "t3": 16
        },
        {
            "aboname": "MARGINALRIDGES",
            "t1": 11,
            "t2": 7,
            "t3": 11
        },
        {
            "aboname": "BUCCOLINGUALINCLINATION",
            "t1": 1,
            "t2": 3,
            "t3": 2
        },
        {
            "aboname": "OCCLUSALCONTACTS",
            "t1": 13,
            "t2": 17,
            "t3": 25
        },
        {
            "aboname": "OCCLUSALRELATIONSHIPPOST",
            "t1": 7,
            "t2": 8,
            "t3": 11
        },
        {
            "aboname": "OVERJETPOSTERIOR",
            "t1": 16,
            "t2": 16,
            "t3": 16
        },
        {
            "aboname": "OVERJETANTERIOR",
            "t1": 4,
            "t2": 9,
            "t3": 5
        },
        {
            "aboname": "INTERPROXIMALCONTACTS",
            "t1": 0,
            "t2": 0,
            "t3": 3
        }
    ]
}
```

*FIG. 31*

Standardized Index Scores

| Total T1 DI+CR score | Total T2 DI+CR score | Total T3 DI+CR score |
|---|---|---|
| 96 | 85 | 148 |
| 81 | 70 | 81 |
| 97 | 83 | 177 |
| 88 | 83 | 83 |
| 92 | 70 | 86 |
| 74 | 60 | 68 |
| 78 | 71 | 224 |
| 52 | 51 | 44 |

*FIG. 32*

Individual and Combined Index Scores

Pre-Treatment Measurements

| # | T1 DI score | T2 DI score | T3 DI score |
|---|---|---|---|
| Overjet (Pre-Treatment) | 0.0 | 2.0 | 2.0 |
| Crowding | 0.0 | 0.0 | 0.0 |
| Overbite | 2.0 | 2.0 | 3.0 |
| Anterior Openbite | 0.0 | 0.0 | 0.0 |
| Lateral Openbite | 0.0 | 0.0 | 0.0 |
| Lingual Posterior Crossbite | 0.0 | 0.0 | 0.0 |
| Buccal Posterior Crossbite | 2.0 | 0.0 | 2.0 |
| Occlusal Relationship (Pre-Treatment) | 0.0 | 0.0 | 0.0 |
| Anomalous Morphology of Tooth Size | 0.0 | 0.0 | 0.0 |
| Midline Discrepancy | 0.0 | 0.0 | 0.0 |
| Generalized Spacing | 0.0 | 0.0 | 0.0 |
| Tooth Transposition | 0.0 | 0.0 | 0.0 |
| Total DI Scores | 4 | 4 | 7 |

Post-Treatment Measurements

| # | T1 CR score | T2 CR score | T3 CR score |
|---|---|---|---|
| Anterior Alignment | 8.0 | 4.0 | 7.0 |
| Posterior Alignment | 18.0 | 16.0 | 15.0 |
| Marginal Ridges | 7.0 | 4.0 | 8.0 |
| Buccolingual Inclination | 0.0 | 0.0 | 0.0 |
| Occlusal Contacts | 11.0 | 18.0 | 13.0 |
| Occlusal Relationship (Post-Treatment) | 16.0 | 11.0 | 14.0 |
| Overjet Posterior | 16.0 | 16.0 | 18.0 |
| Overjet Anterior | 8.0 | 12.0 | 0.0 |
| Interproximal Contacts | 2.0 | 0.0 | 3.0 |
| Total CR Scores | 84 | 79 | 76 |

*FIG. 33*

AUTOMATED SYSTEM AND METHODS TO EVALUATE PLANNED TREATMENT PERFORMANCE AND REAL TREATMENT PERFORMANCE USING THREE-DIMENSIONAL VIRTUAL DENTAL MODELS

FIELD OF THE INVENTION

The present invention is directed towards orthodontic treatment, especially orthodontic treatment using clear aligners and the prerequisite virtual orthodontic treatment plan.

BACKGROUND OF THE INVENTION

Orthodontic treatment performance can be influenced by a wide range of factors, such as patient-specific treatment conditions, diagnostics, dental health and hygiene, treatment protocol parameters, planned treatment complexity, treatment plan compliance, manufactured aligner quality, and real treatment performance. These factors, along with others, create a challenging environment to evaluate real treatment performance systematically and objectively in comparison to planned treatment performance. There is therefore a need to provide more efficient, precise, and accurate evaluations of real treatment performance by minimizing or eliminating manually performed measurements and physical materials.

SUMMARY OF THE INVENTION

One embodiment of this invention pertains to a method of automatically determining orthodontic treatment plan scores and treatment performance scores using three-dimensional (3D) virtual models, the method including the steps of obtaining, in a computer-implemented software system, at least one of virtual stage models or dental mesh models. Embodiments may also include processing, in the computer-implemented software system, the at least one of virtual stage models or dental mesh models to create one or more composite stage models. Embodiments may also include determining, in the computer-implemented software system, virtual measurement values from geometries in at least one of the virtual stage models or the one or more composite stage models.

In one embodiment, the method further includes applying, in the computer-implemented software system, index classifiers to virtual measurement values. Embodiments may also include outputting, from the computer implemented software system, planned treatment performance scores and real treatment performance scores based on the applied index classifiers to evaluate real treatment performance.

In one embodiment, the obtaining step includes obtaining virtual stage models which define an orthodontic virtual treatment plan from a non-transitory computer readable medium. Embodiments may also include a set of virtual stage models defining the initial positions of anatomical objects and constructed objects within the upper and lower dental arches. Embodiments may also include a set of virtual stage models which define the planned positions of anatomical objects and constructed objects within the upper and lower dental arches.

In one embodiment, the obtaining step includes obtaining dental mesh models of the upper and lower dental arches from a non-transitory computer readable medium. In some embodiments, the dental mesh models define the real positions of anatomical geometries, of the upper and lower dental arches, during a treatment stage. In some embodiments, the dental mesh models define the real positions of anatomical geometries, of the upper and lower dental arches, during a retention stage.

In one embodiment, the processing step includes overlaying dental mesh models onto virtual stage models. In some embodiments, the processing step may include repositioning objects (e.g., tooth objects) within the virtual stage models to match the real tooth positions of geometries represented by the dental mesh models. In some embodiments, the processing step may include generating a composite stage model of an upper dental arch and a lower dental arch. In one embodiment, the composite stage model(s) defines real positions of objects within the upper and lower dental arches.

In one embodiment, the determining step includes performing a series of automated virtual measurements, using virtual stage models and the one or more composite stage models. Embodiments may also include virtual measurements that are performed on geometries within anatomical objects representing tooth structures and positions. Embodiments may also include virtual measurements that are performed on geometries defining anatomical objects which represent periodontal tissues and positions.

In one embodiment, the applying step includes applying index classifiers to individual measurement values, a group of measurement values, or a combination thereof. In some embodiments, the applied classifiers are defined by the Discrepancy Index (DI). In some embodiments, the applied classifiers are defined by the Cast-Radiograph (CR) evaluation. In some embodiments, the applied classifiers are defined by the Periodontal Screening and Recording Index (PSR), the Index of Recession (IR), the Palatal Recession Index (PR), or a combination thereof.

In one embodiment, the applying step includes combining total Discrepancy Index (DI) scores with total Cast-Radiograph (CR) scores to create standardized index scores for each set of the measured at least one of the virtual stage models or the one or more composite stage models. In some embodiments, standardized index scores for an initial stage virtual stage model define planned treatment baseline scores and treatment performance baseline scores. In some embodiments, standardized index scores for a planned stage virtual stage model define planned treatment performance scores. In some embodiments, standardized index scores for a composite virtual stage model define real treatment performance scores.

In one embodiment, the outputting step includes outputting and/or automatically outputting individual measurement scores, total index scores, and standardized index scores to a non-transitory computer readable medium.

In one embodiment, the upper and lower arch virtual stage models contain segmented objects and metadata defined by the treatment plan. In some embodiments, the segmented objects may be formed by anatomical geometries or constructed geometries. Embodiments may also include anatomical geometries representing tooth structures and gingival tissues.

In one embodiment, constructed geometries are included to represent non-anatomical objects. In some embodiments, metadata contains information not expressly defined by the geometries of the virtual stage models. Embodiments may also include a dental mesh model of an upper and lower arch that is obtained at a treatment stage or a retention stage of orthodontic treatment.

In one embodiment, a dental mesh model is generated from a three-dimensional scanner. In some embodiments, the dental mesh model may be generated from a physical mold of the patient's teeth. In some embodiments, the dental mesh model may be generated from a composite stage model derived from a combination of diagnostic dental mesh models, planned virtual stage models, and two-dimensional (2D) images depicting the positions of real anatomical geometries of the upper and lower arch.

Another embodiment pertains to a computer-implemented software system for automatically determining orthodontic treatment scores using virtual three-dimensional (3D) dental models. The system comprises an input module configured to obtain and process at least one of virtual stage models or virtual dental mesh models. Embodiments also include a processing module configured to generate one or more composite stage models from the at least one of virtual stage models or dental mesh models.

In one embodiment, the system further includes a measurement module configured to determine virtual measurement values from geometries in at least one of the virtual stage models or the one or more composite stage models. Embodiments may also include a scoring module configured to apply index classifiers to virtual measurement values. Embodiments may also include an export module configured to output planned treatment performance scores and real treatment performance scores based on the applied index classifiers.

In one embodiment, the input module is configured to obtain the at least one of virtual stage models or dental mesh models from a non-transitory computer readable medium via an user interface. In some embodiments, the input module may be configured to obtain the at least one of virtual stage models or dental mesh models by automated retrieval instructions within a virtual computing environment.

In one embodiment, a set of virtual stage models defines initial positions of anatomical objects and constructed objects within upper and lower dental arches. In another embodiment, a set of virtual stage models defines planned positions of anatomical objects and constructed objects within upper and lower dental arches.

In one embodiment, the input module is further configured to obtain dental mesh models of upper and lower dental arches from a non-transitory computer readable medium. In an embodiment, the dental mesh models define real positions of anatomical geometries, of the upper and lower dental arches, during any treatment stage. In another embodiment, the dental mesh models define real positions of anatomical geometries, of the upper and lower dental arches, during a retention stage.

In one embodiment, the processing module is configured to overlay dental mesh models onto virtual stage models. In one embodiment, the processing module is further configured to reposition objects within virtual stage models to match real positions of geometries within dental mesh models. In one embodiment, the processing module is configured to generate a composite stage model of an upper dental arch and a lower dental arch.

In some embodiments, the measurement module is configured to perform a series of automated virtual measurements, using virtual stage models and the one or more composite stage models. In one embodiment, the virtual measurements are performed on at least one of (i) geometries within anatomical objects representing tooth structures and positions or (ii) geometries defining anatomical objects which represent periodontal tissues and positions.

In some embodiments, the scoring module is configured to apply index classifiers to individual measurement values, a group of measurement values, or some combination thereof. In one embodiment, the applied index classifiers are defined by at least one of the Discrepancy Index (DI) or the Cast-Radiograph (CR) evaluation. In one embodiment, the scoring module is further configured to combine total Discrepancy Index scores with total Cast-Radiograph scores to create standardized index scores for each set of the measured at least one of the virtual stage models or the one or more composite stage models. In some embodiments, standardized index scores for an initial stage virtual stage model define planned treatment baseline scores and treatment performance baseline scores. In some embodiments, standardized index scores for a planned stage virtual stage model define planned treatment performance scores. In some embodiments, standardized index scores for a composite virtual stage model define real treatment performance scores.

In some embodiments, the export module is configured to automatically output measurement scores, total index scores, and standardized index scores to a non-transitory computer readable medium.

Another embodiment of this invention pertains to a non-transitory computer-readable medium configured to process and display treatment scoring information in a graphical user-interface module. In some embodiments, a processor executes functions to display scores and patient information. Embodiments may also query previous scoring data and information. Embodiments may also filter, group and sort scoring data and information. Embodiments may also include output scoring data and information.

In one embodiment, with respect to a display function, standardized index scores, of all evaluated cases, are included, which are presented or accessed via a graphical (or interactive) user-interface (GUI). Embodiments may also include, with respect to a display function, measurement scores and total index scores of an evaluated case, which are presented or accessed via a graphical (or interactive) user-interface (GUI). Embodiments may also include, with respect to a query function, previous measurement scores, total index scores, and standardized index scores which are accessed and stored.

In one embodiment, scoring data and information are selected and arranged by a user input (e.g., via a filter, group and sort function). Embodiments may also include, with respect to an output function, scoring data and information which is exported from the non-transitory computer-readable medium. Embodiments also include, with respect to an output function, scoring data and information that is automatically exported from the non-transitory computer-readable medium.

BRIEF DESCRIPTION OF THE FIGURES

The accompanying drawings, which are incorporated into and form a part of the specification, illustrate one or more embodiments of the present invention. In combination with the provided descriptions, the drawings serve to explain the principles of the invention. The drawings illustrate embodiments of the invention and should not be considered as limiting the scope of the invention.

FIG. 4*b* is an illustration of an anatomical object naming (or labeling) convention which is automatically applied by a computer implemented module, within the treatment planning software, to define segmented objects according to one embodiment of the invention.

FIG. 8 is a list summarizing the discrepancy index (DI) and cast-radiograph (CR) measurements according to one embodiment of the invention.

FIG. 29 is an illustration of the standard discrepancy index (DI) score sheet according to one embodiment of the invention.

FIG. 30*a* is an illustration of the standard cast-radiograph (CR) classification chart according to one embodiment of the invention.

FIG. 31 is an illustration of a local output score data file according to one embodiment of the invention.

FIG. 32 is an illustration of the standardized index score output according to one embodiment of the invention.

FIG. 33 is an illustration of the individual and total index score outputs according to one embodiment of the invention.

DETAILED DESCRIPTION OF THE INVENTION

Figure 1:
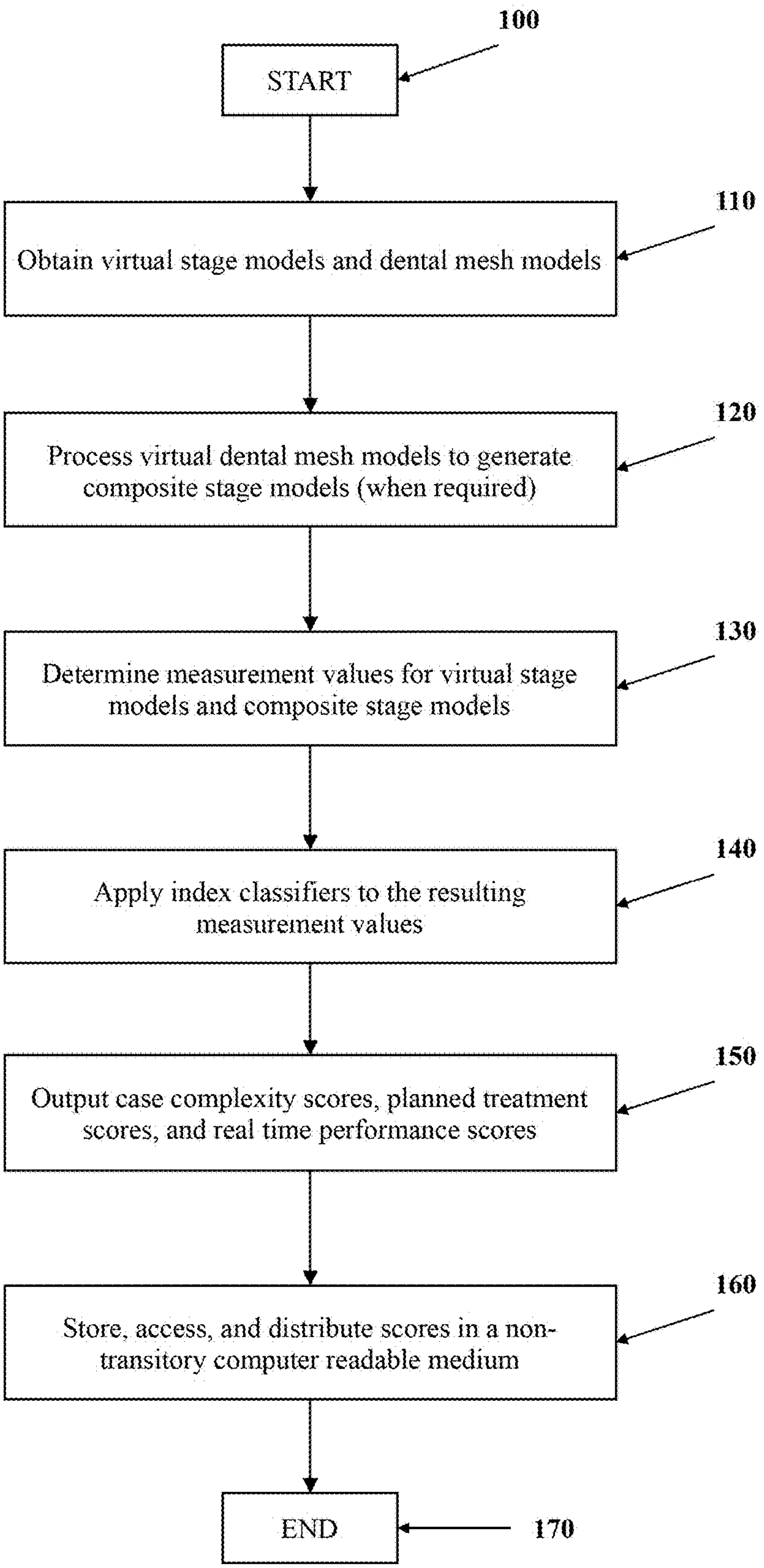
FIG. 1 is a flowchart illustrating a method of automatically determining orthodontic treatment plan scores and performance scores, according to some embodiments of the present disclosure.

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure are intended to be illustrative, and not restrictive.

Throughout the specification and claims, the following terms take the meanings explicitly associated herein, unless the context clearly dictates otherwise. The phrases “in one embodiment,” “in an embodiment,” and “in some embodiments” as used herein do not necessarily refer to the same embodiment(s), though they may. Furthermore, the phrases “in another embodiment” and “in some other embodiments” as used herein do not necessarily refer to a different embodiment, although they may. All embodiments of the disclosure are intended to be combinable without departing from the scope or spirit of the disclosure.

As used herein, the term “based on” is not exclusive and allows for being based on additional factors not described, unless the context clearly dictates otherwise. In addition, throughout the specification, the meaning of “a,” “an,” and “the” include plural references. The meaning of “in” includes “in” and “on.”

As used herein, terms such as “comprising” “including,” and “having” do not limit the scope of a specific claim to the materials or steps recited by the claim.

As used herein, terms such as “consisting of” limit the scope of a specific claim to the materials and steps recited by the claim.

All prior patents, publications, and test methods referenced herein are incorporated by reference in their entireties.

The present invention is directed towards orthodontic treatment, especially orthodontic treatment using clear aligners and the prerequisite virtual orthodontic treatment plan. Clear aligners provide an alternative to traditional orthodontic bracket and wire systems. A clinician prescribes a series of aligners, which generally are placed over the teeth but not adhesively secured to them. Each manufactured aligner is worn in sequential order starting with stage one (1) through the last stage (xx) of the prescribed orthodontic treatment plan, or until a preferred outcome is achieved.

Each aligner represents a stage of orthodontic treatment. Stage zero (0) represents the initial tooth positions of a pre-treatment orthodontic case. Each subsequent stage represents planned tooth movement by application of gentle, continuous force generated by a worn aligner. The last stage of a virtual treatment plan defines the final planned tooth positions of the treated upper dental arch and lower dental arch. A virtual treatment plan is defined by the virtual stage models representing the baseline tooth positions at stage (0) and the planned tooth positions representing the planned tooth movement represented in stage one (1) through the last stage (xx). Aligners are manufactured by 3D printing a physical mold of an input virtual stage model. Next, a poly-layered plastic material is usually thermoformed onto the mold using specialized equipment and removed from the mold along a defined trim path. The aligners are also polished then bagged for fulfillment.

Virtual orthodontic treatment plans are typically generated using a collection of diagnostic records such as: patient medical history and demographics, intraoral and extraoral photographs, radiographs, cone beam computed tomography scans (CBCT), three-dimensional (3D) virtual dental mesh models, or some combination thereof. Digital impressions of the upper and lower dental arches representing pre-treatment, are obtained to define the initial, or baseline, tooth positions before treatment.

Diagnostic virtual dental mesh models, virtual point clouds models, or a combination thereof, are imported into a computer implemented software system designed to allow a user, also known as a technician, to create a virtual treatment plan using digital tools and aided by automated software functions. Generally, a series of automated functions and mesh rendering techniques are applied to the obtained diagnostic virtual mesh models to construct a stage zero (0) virtual stage model. Common techniques include: segmenting and labeling the teeth and gingiva to create named 3D objects, surface sculpting or modeling, and triangle decimation.

Once the virtual dental mesh models are processed into stage zero (0) virtual stage files, a technician manually adjusts each tooth, within the virtual treatment planning software, from the initial tooth positions to a position representing a preferred treatment outcome. Next, the total planned tooth movement is automatically divided into stages, beginning with stage one (1), and ending with the last stage (xx). The number of treatment stages is calculated as defined by the configured instructions, parameters, and per stage tooth movement thresholds. One upper arch virtual stage model and one lower arch virtual stage model, comprising named 3D objects, are generated for each stage. These virtual stage models define the planned tooth positions of the upper and lower dental arch at the completion of a stage of the corresponding orthodontic treatment.

Generally, the final step in the process of generating virtual stage models for aligner manufacturing is the merge and export process. Generally, the named objects comprising a virtual stage model are merged into one 3D mesh model. Virtual stage models and additional aligner manufacturing specification data are then exported to a non-transitory computer-readable storage medium.

While there are published guidelines and best practices to direct orthodontic treatment planning methodologies, preference-based orthodontic prescription treatment protocols guided by clinical experience are overwhelmingly pervasive throughout the orthodontic field. In the present disclosure, a virtual treatment planning protocol is defined as a set of standard orthodontic treatment parameters, thresholds, and considerations. Virtual treatment planning protocols are applied as directed by a provider, a group of providers, or some combination thereof. Treatment protocols generally define, order, and prioritize tooth movement parameters and associated orthodontic considerations to be implemented in a virtual treatment plan. Additionally, they are commonly derived from treatment methodologies and clinical experience and typically applied across all treatment cases managed by a provider or group of providers. In practice, treatment protocols often vary significantly between providers, a group of providers, or a combination thereof.

As discussed above, orthodontic treatment performance can be influenced by a wide range of factors, such as patient-specific treatment conditions, diagnostics, dental health and hygiene, treatment protocol parameters, planned treatment complexity, treatment plan compliance, manufactured aligner quality, and real treatment performance. These factors, along with others, create a challenging environment to systematically and objectively evaluate real treatment performance in comparison to planned treatment performance. Additionally, the resulting values must be standardized across a wide range of orthodontic case types, baseline case complexities, treatment objectives, and treatment protocols to account for a range of orthodontic treatment methodologies. Moreover, functional challenges in scheduling, patient compliance, and cost, among other factors, is a limiting factor in the scale at which an office is able, or willing to obtain digital impressions of a patient’s upper and lower dental arches during the orthodontic treatment and retention phases, which limits the collection of objective data that could be applied to inform treatment planning protocols.

Figure 30B:
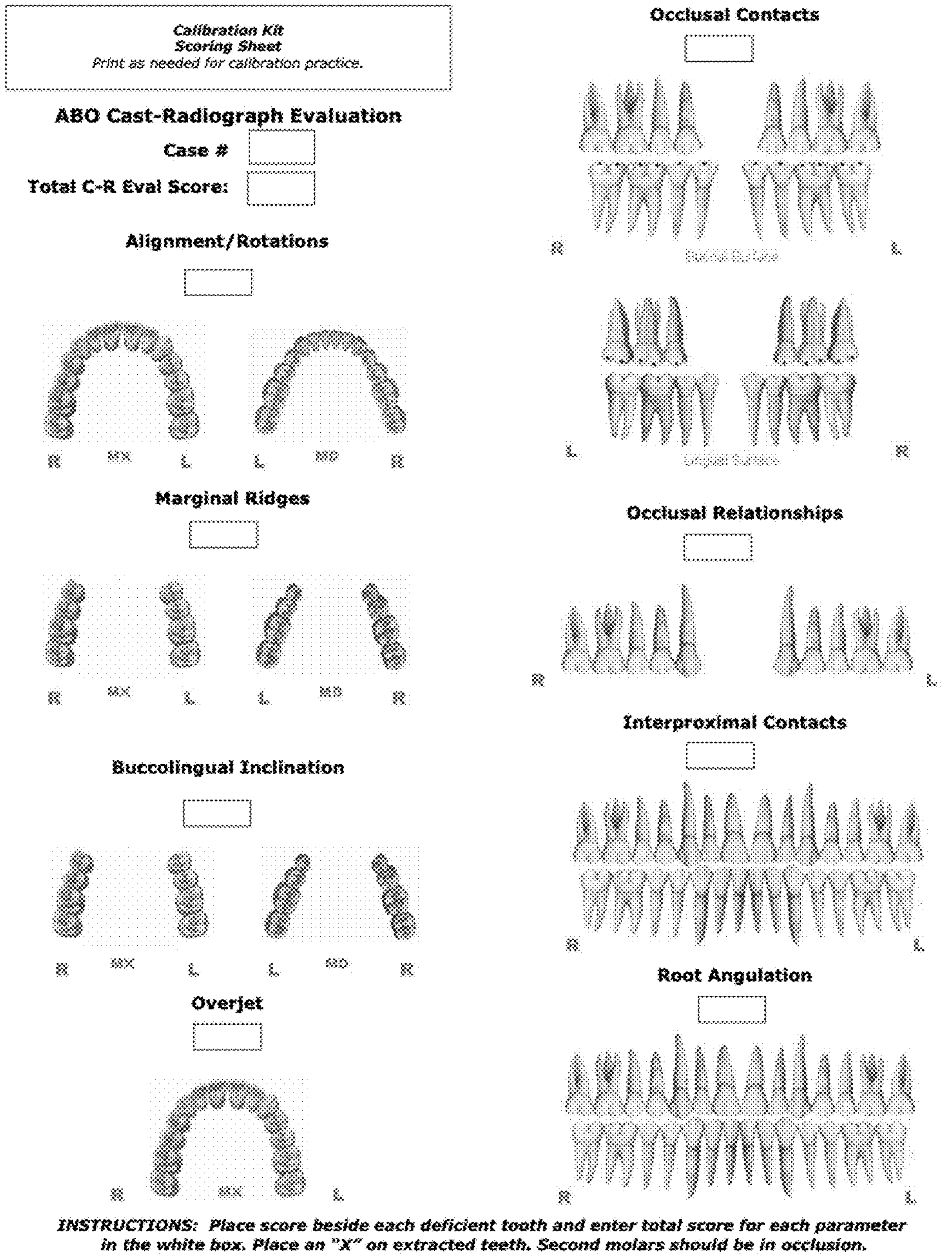
FIG. 30*b* is an illustration of the standard cast-radiograph (CR) score card according to one embodiment of the invention.

Although standardized indexes and evaluation methods were published by the American Board of Orthodontics (ABO) (see, e.g., FIGS. 29, 30*a* and 30*b*), it is rare for a practice to integrate these methods into their orthodontic treatment workflow due to the materials, labor, advanced planning, and skill required to conduct these assessments at a cost-effective scale. Discrepancy Index (DI) and Cast-Radiograph evaluation (CR) scores are applied to an orthodontic treatment case by a certified clinician who performs a series of manual measurements on 3D printed or plaster upper and lower arch dental models, with a customized set of tools that is ordered directly from the ABO organization. The defined measurement techniques require great calibration and clinical knowledge in guiding the placement of the measurement tools and accurately determining small-scale measurement values on the 3D printed or plaster models. Moreover, inter-examiner and intra-examiner calibration is difficult to achieve and maintain. These factors combine to stem the adoption and implementation of standardized treatment performance indices and the associated measurement methods as they currently exist.

While tools for manipulating virtual 3D objects are well-developed and clear aligner orthodontic treatment plans are manufactured from virtual stage models made of named objects, these manual measurement techniques performed on physical dental models have not yet been digitally applied to virtual stage models. The disclosed computer implemented software system and methods result in more efficient, precise, and accurate DI and CR evaluations by eliminating manually performed measurements and physical materials. Thus, the disclosed computer implemented software system and methods improve upon the feasibility, speed, accuracy, and precision of the published Discrepancy Index (DI), Cast-Radiograph (CR) and periodontal disease evaluation methods. Furthermore, the present disclosure builds upon the indices by establishing methods to obtain, process, and determine measurement values for virtual stage models representing a stage of planned orthodontic treatment, where the ABO methods are applied to baseline and treatment outcome models.

System and Method Summary

The present invention, in embodiments, provides systems and methods for automatically determining orthodontic treatment plan scores and treatment performance scores using three-dimensional (3D) virtual dental models. An object of the present disclosure is to classify pre-treatment case complexity, planned treatment performance, real treatment performance, or a combination thereof using two or more sets of virtual stage models. To accomplish this, virtual stage models, from a virtual treatment plan are obtained and processed, measurement values are determined, index classifiers are applied to the measurement values, additional scores are computed, and the results are output.

For example, FIG. 1 provides a flowchart illustrating a method of automatically determining orthodontic treatment plan scores and performance scores, according to some embodiments of the present disclosure. As shown in the embodiment of FIG. 1, the process starts at step 100 and begins with obtaining virtual stage models and/or virtual dental mesh models (see, e.g., FIG. 6) at step 110. Next, at step 120, any obtained virtual dental mesh models are processed to generate composite stage models (when required) (see, e.g., FIG. 7). Thereafter, at step 130, measurement values are determined for the obtained virtual stage models and/or the generated composite stage models. At step 140, index classifiers are applied to the resulting measurement values from step 130. Next, at step 150, case complexity scores, planned treatment scores, and real time performance scores are output, and thereafter, at step 160, the scores from step 150 are stored, accessed and/or distributed in a non-transitory computer readable medium. The exemplary method of FIG. 1 then ends at step 170.

Figure 5:
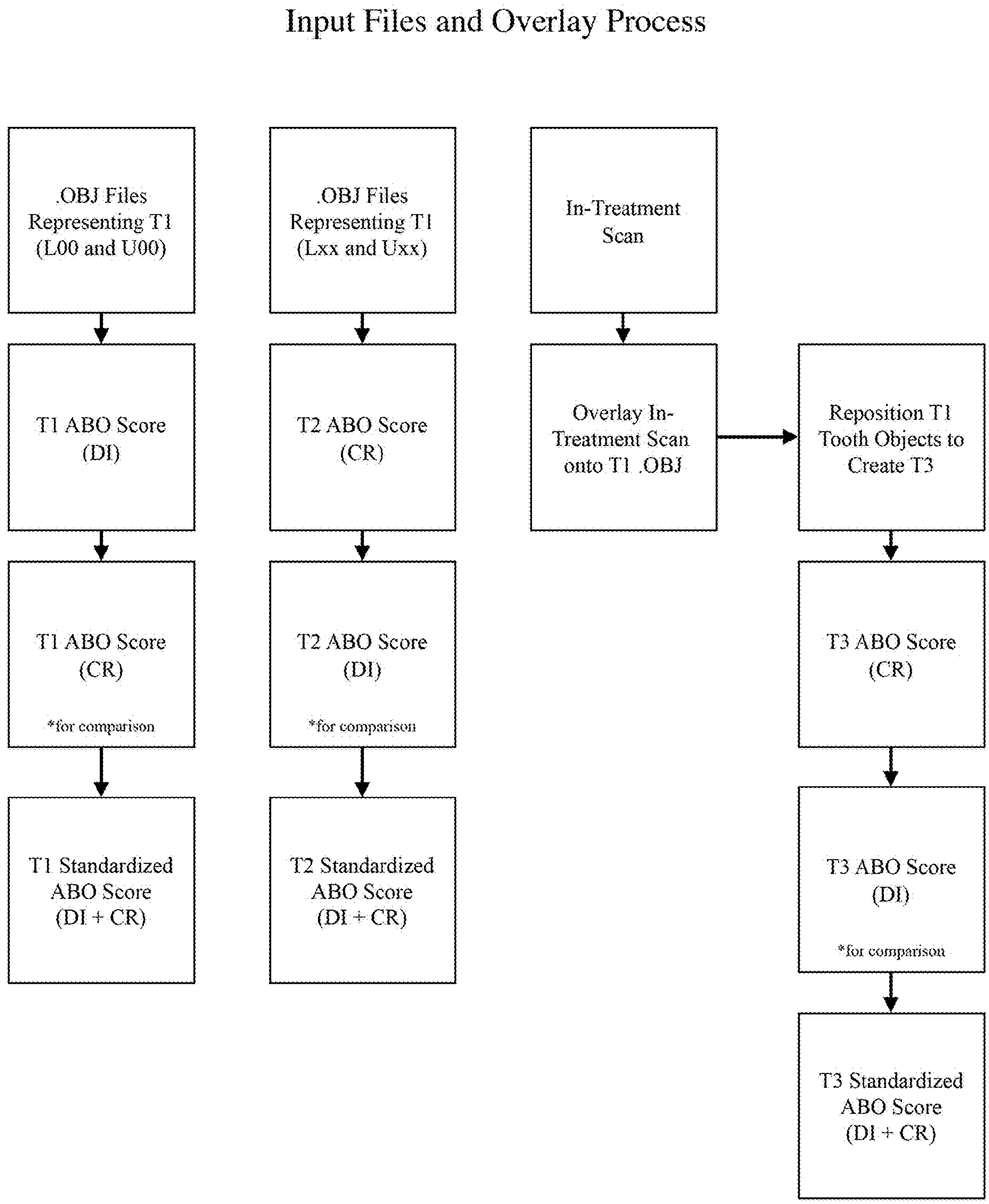
FIG. 5 is an illustration of obtained input files and a composite virtual stage model generation process according to one embodiment of the invention.
Figure 7:
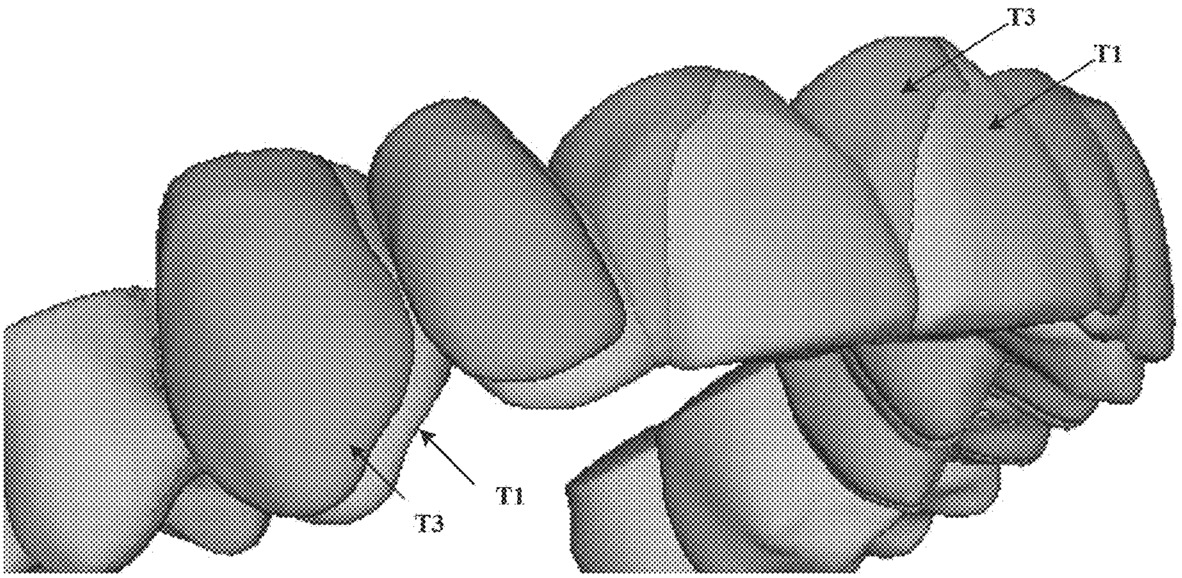
FIG. 7 is an illustration of a dental mesh model overlaid onto a virtual stage model to generate a virtual composite stage model according to one embodiment of the invention.

FIG. 5 is an illustration, according to an embodiment of the invention, of the obtained input files from, e.g., step 110 of FIG. 1 and the composite virtual stage model generation process, as in, e.g., step 120 of FIG. 1. FIG. 7 is an illustration, according to an embodiment of the invention, of a virtual dental mesh model overlaid onto a virtual stage model, which is used to generate a virtual composite stage model, as in, e.g., step 120 of FIG. 1.

Another embodiment of this invention pertains to a computer-implemented software system for automatically determining real treatment performance scores using 3D models. The system comprises an input module configured to obtain and process virtual stage models and virtual dental mesh models. Embodiments also include a processing module configured to generate composite stage models from the dental mesh models and virtual stage models. In one embodiment, the system further includes a measurement module configured to determine virtual measurement values from geometries in the virtual stage models and composite stage models. Embodiments may also include a scoring module configured to apply virtual measurement values to index classifiers. Embodiments may also include an export module configured to output planned treatment performance scores and real treatment performance scores.

Figure 34:
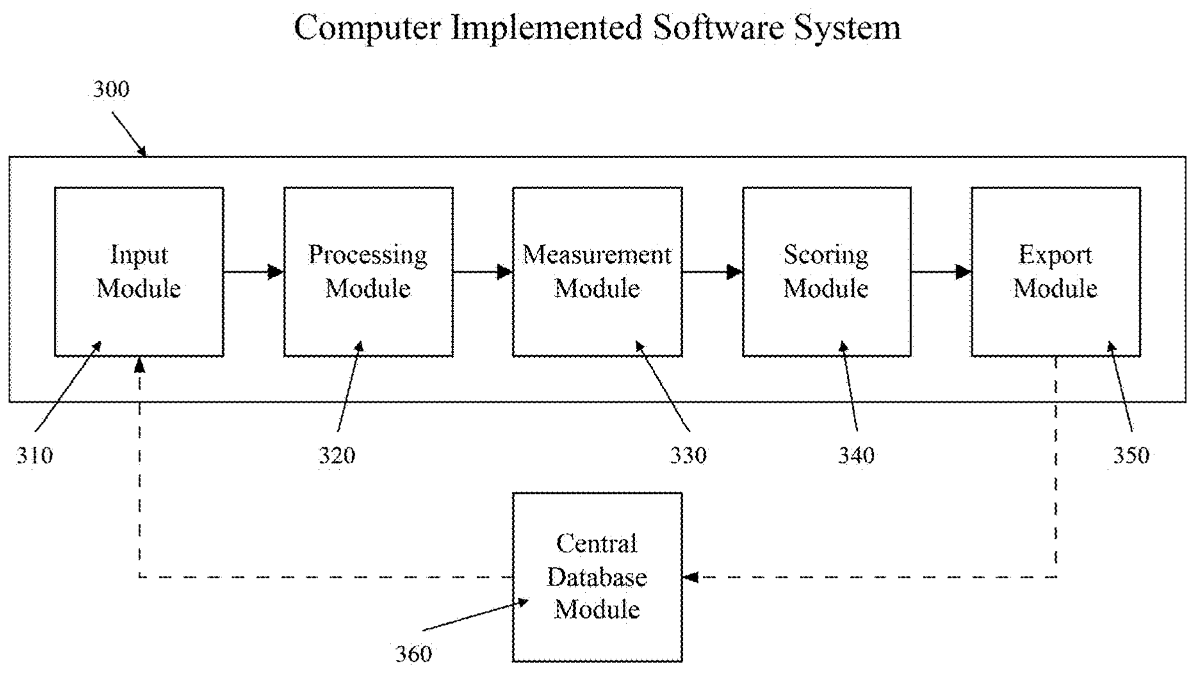
FIG. 34 is a block diagram illustrating a computer-implemented software system, according to some embodiments of the present disclosure.

For example, FIG. 34 provides a block diagram illustrating a computer-implemented software system, according to some embodiments of the present disclosure. As shown in the embodiment of FIG. 34, the computer-implemented software system (300) includes (i) an input module (310) configured to obtain and process virtual stage models and virtual dental mesh models, (ii) a processing module (320) configured to generate composite stage models from the dental mesh models and virtual stage models, (iii) a measurement module (330) configured to determine virtual measurement values from geometries in the virtual stage models and composite stage models, (iv) a scoring module (340) configured to apply virtual measurement values to index classifiers, and (v) an export module (350) configured to output planned treatment performance scores and real treatment performance scores. As further shown in the embodiment of FIG. 34, the computer-implemented software system (300) further includes a central database module (360), which is further described below, which is in communication with the system via, e.g., the input module (310) and/or the export module (250), and is configured to store and/or provide data.

Treatment Phases

Figure 2:
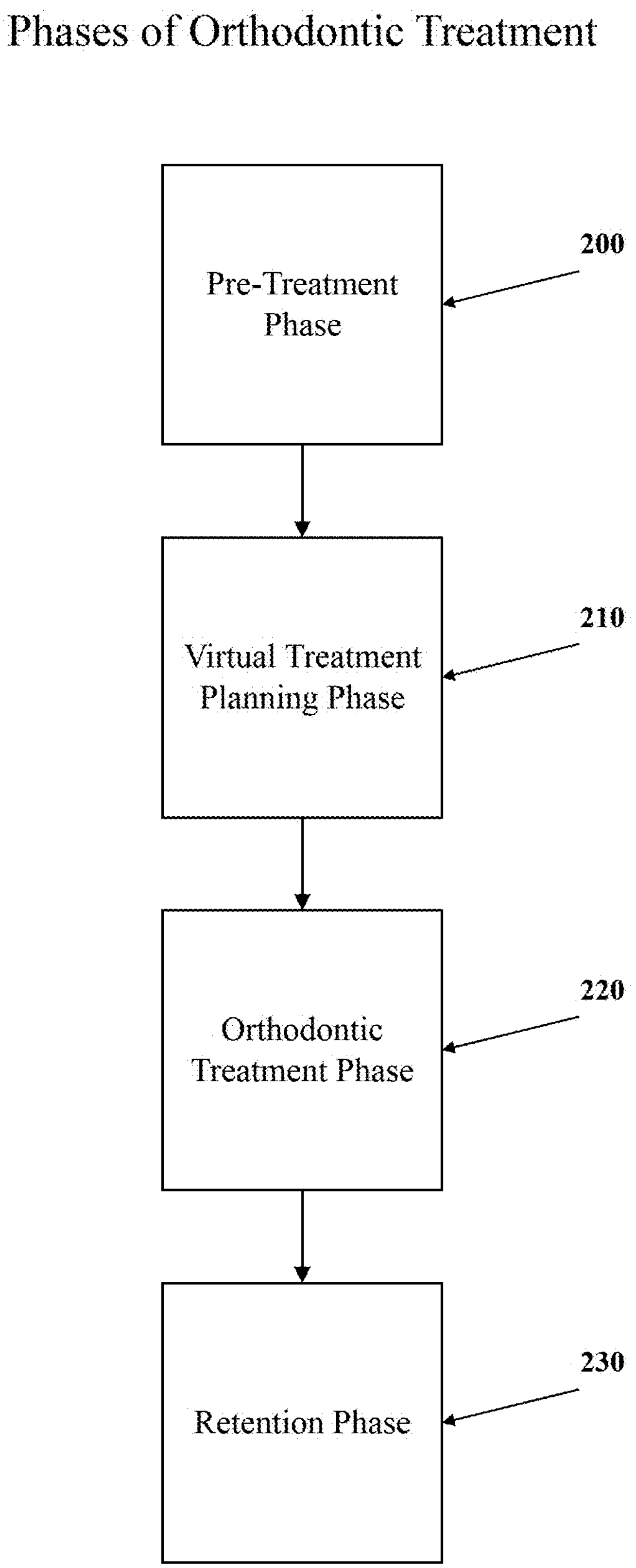
FIG. 2 is a chart illustrating the phases and stages of orthodontic treatment according to one embodiment of the invention.
Figure 6:
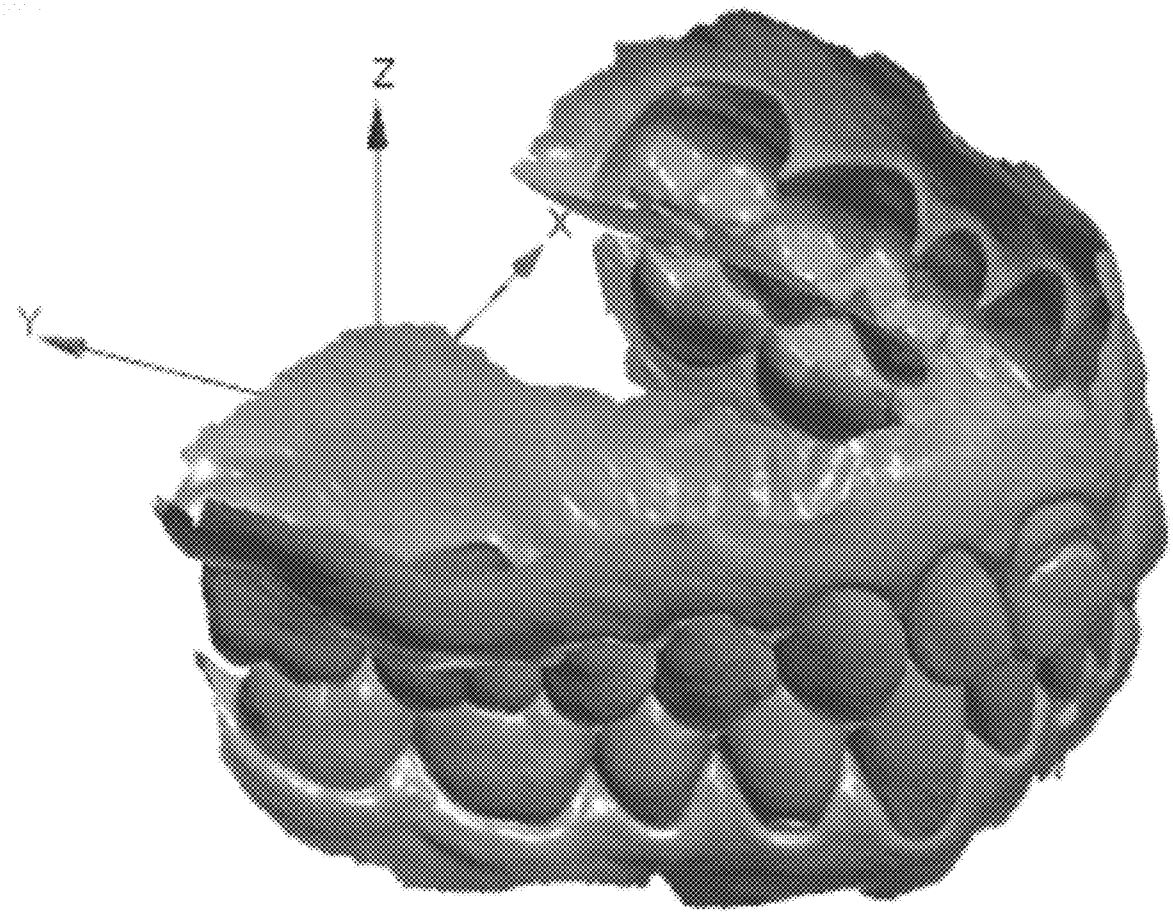
FIG. 6 is an illustration of a dental mesh model according to an embodiment of the invention.

As it pertains to the present disclosure and as illustrated in FIG. 2, orthodontic treatment includes four (4) phases: the pre-treatment phase (200), the virtual treatment planning phase (210), the orthodontic treatment phase (220), and the retention phase (230). The pre-treatment phase (200) comprises obtaining diagnostic virtual dental mesh models, patient demographics, and relevant medical history, along with identifying a preferred clinical outcome. As applied in the present disclosure, the term "virtual dental mesh model" describes a digital representation of an upper dental arch, lower dental arch, or some combination thereof. For example, FIG. 6 is an illustration of a dental mesh model according to an embodiment of the invention. Similarly, a set of dental mesh models encompasses both the upper dental arch model and lower dental arch model which are oriented relative to the relationship between the occlusal surfaces of the tooth objects comprising the two meshes.

Mesh Elements

As discussed above, virtual dental mesh models are the foundation of the aligner production process, and similarly, they are a critical component of the disclosed system and methods. Dental mesh models represent the same set of anatomy as the virtual stage files generated during the treatment planning process, but the underlying differences in data format and components are significant to a few key aspects of this system. Most significantly, virtual dental mesh models are considered one object with one continuous border comprised of many polygons. Whereas, virtual stage models are comprised of multiple segmented objects, each independent of the other objects, as defined by segmented borders. To better understand the disclosed systems and methods, detailed descriptions of mesh elements, unstructured meshes, and point cloud to mesh processing are provided as follows. A polygon mesh is a collection of connected vertices, edges, and faces which defines the shape of one virtual object. In the present disclosure, the term "virtual dental mesh model" is used to further specify the functional attributes and nature of a generated polygon mesh. Objects created with polygon meshes comprise a combination of five (5) basic elements: vertices, edges, faces, polygons, and surfaces. Most commonly, only vertices, edges, and either faces or polygons are stored within the objects. As applied in the present disclosure, faces are most accurately defined as a closed set of edges, in which a triangle face has three edges and a quad face has four edges. Likewise, a polygon is a coplanar set of faces. In systems supporting multi-sided faces, polygons and faces are equivalent. However, the majority of 3D scanning hardware and software only support three-sided faces or four-sided faces, where polygons are defined by one or more faces.

Unstructured Mesh

A polygonal mesh may be considered an unstructured grid or undirected graph, containing additional properties of geometry, shape and topology. Mesh models are created using computer implemented algorithms, applied with human guidance, to capture physical object data using a computer implemented graphical user interface (GUI). In geometric terms, dental mesh models are unstructured meshes, in which elements may be connected to each other in irregular patterns. They are also triangulations, or a subdivision of a planar object into triangles; and by extension, the subdivision of a higher-dimension geometric object into simplices which are often arranged in simplicial complexes that partition the geometric input domain. Mesh cells are used as discrete local approximations of the larger domain.

Point Cloud to Mesh

When digitizing a physical object, such as, e.g., an upper dental arch, lower dental arch, or both, the captured data is typically arranged in the form of a point cloud. A point cloud is a discrete set of data points in space where each point position is defined by a set of Cartesian coordinates (X, Y, Z). Point clouds are generally produced by 3D scanners, industrial computed tomography (CT), or photogrammetry software, to measure and record tens of thousands of points on the external surfaces of objects around them. They can be aligned as one object with 3D mesh models, other point clouds, or to an existing model for comparison, evaluation, and manipulation. In accordance with embodiments described herein, point clouds are most commonly converted to polygon or triangle mesh models prior to export via computer implemented software modules configured to perform a surface reconstruction process. These mesh models, and the geometries that define them are considered a "raw" data format, suitable for representing the form of a dental arch, but still requiring further processing to determine measurement values in relation to specific tooth and gingival anatomy within the measured dental arch. This processing step generally occurs within a treatment planning software, where importing the virtual dental mesh models marks the beginning of the virtual treatment planning phase. The terms: mesh model, virtual mesh model, and virtual dental mesh model are applied in the present disclosure to most accurately represent a number of commonly used terms, such as, e.g., digital impression, intraoral scan, scan, dental impression, digitized impression, generated virtual impression, and other similar terminology.

Stage Model Elements

Virtual stage models (see, e.g., FIG. 3) differ from virtual dental mesh models in that they are comprised of multiple segmented anatomical objects, constructed objects, or a combination thereof; each with a continuous border and applied label. However, the objects are comprised of polygons which generally maintain accuracy to their original mesh models. Functionally, the named objects within virtual stage models facilitate the automated application of measurements on represented teeth by providing object labels for determined value to tooth associations. A brief description of constructed objects and object labels is provided below.

Constructed Objects

Figure 3:
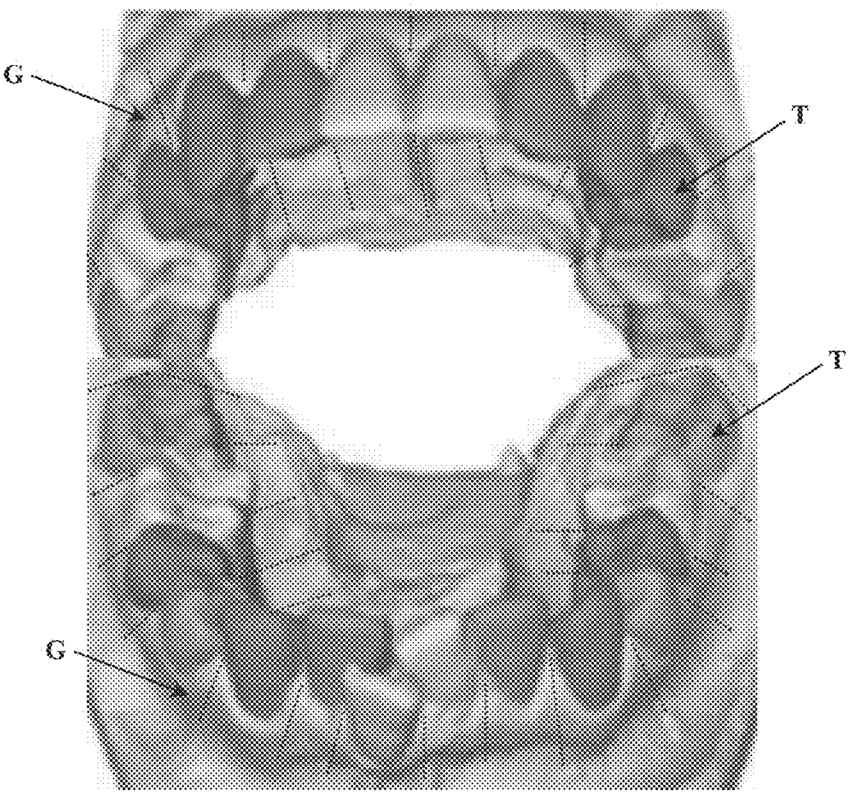
FIG. 3 is an illustration of a segmented virtual stage model with tooth objects (T) and gingiva objects (G) labeled according to one embodiment of the invention.

In some embodiments, the upper and lower arch virtual stage models are made of segmented objects and metadata, which are defined within the virtual treatment plan. The segmented objects are either a group of anatomical geometries or a group of constructed geometries. Anatomical geometries represent tooth structures and gingival tissues, whereas constructed geometries represent non-anatomical objects such as orthodontic appliances. In some embodiments, the metadata may contain information not expressly defined by the geometries of the virtual stage models. For example, FIG. 3 illustrates a segmented virtual stage model, according to one embodiment of the invention, with tooth objects (T) and gingiva objects (G) labeled with coloring/shading and dashed lines, respectively.

Object Labels

Figure 4A:
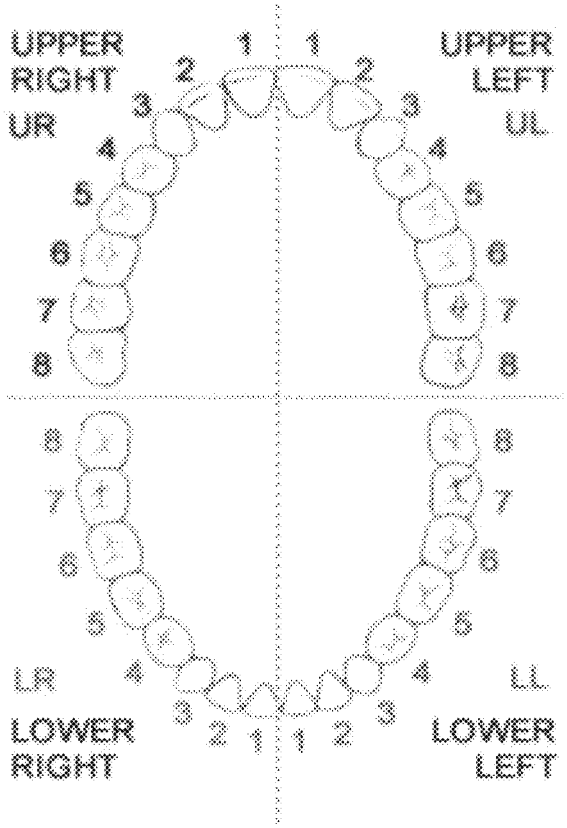
FIG. 4*a* is an illustration of the Palmer dental notation system used in the anatomical object naming (or labeling) convention which is automatically applied by a computer implemented module, within the treatment planning software, to define segmented objects according to one embodiment of the invention.

Segmented teeth, segmented gingiva, and orthodontic appliances are labeled as individual 3D objects. Generally, tooth objects are assigned tooth identification labels according to a dental tooth numbering convention such as, e.g., the letters and numbers system, the Palmer system, or any combination thereof (see, e.g., FIG. 4*a*). Gingiva objects are labeled according to relative tooth region, or as one combined gingival region per dental arch (see, e.g., FIG. 4*b*). When present, orthodontic appliance objects, such as, e.g., attachments, bite ramps, and virtual filler, are assigned object labels, which are also maintained when stage models are exported from a virtual treatment plan.

Virtual Treatment Planning Phase

In the virtual treatment planning phase (see, e.g., phase 210 of FIG. 2), the processing step described above generally comprises software-assisted object segmentation and identification functions within a virtual treatment planning software, where stage (00) virtual stage models are created from the imported virtual dental mesh models. In general, the dental mesh models are segmented into tooth and gingiva objects (see, e.g., FIG. 3), and labels are applied to the segmented anatomical objects comprising the upper and lower dental arch (see, e.g., FIGS. 4 and 4*b*). At this point, the segmented anatomical objects become named objects. A trained user determines the final planned tooth positions, or planned treatment performance, by virtually adjusting the tooth objects to reflect a preferred clinical outcome within a virtual treatment planning software user interface. Final planned tooth positions are guided by a series of clinical treatment protocols, which outline optimal final tooth positions and tooth movement priorities and parameters, in addition to several additional orthodontic treatment planning considerations. Treatment protocols are interpreted and applied to generate a virtual treatment plan by a trained and calibrated technician.

Subsequently, total planned movement is determined automatically per tooth and by planned movement type, measured from initial tooth positions to final planned tooth positions defined by the first stage and last stage virtual stage models. The determined values are then divided across a number of virtual treatment plan stages to create a virtual treatment plan. The total number of virtual treatment plan stages is automatically determined by a module within the treatment planning software configured to follow a prioritized set of configured parameters. As a result, upper and lower arch virtual stage models, comprising named objects, are generated for each stage of the virtual treatment plan. Planned tooth positions are defined by the named objects within each set of virtual stage models comprising a virtual treatment plan. The planned tooth movement in each stage of a virtual treatment plan, is determined by calculating the delta between the planned tooth positions of the previous stage and the planned tooth positions of the assessed stage. After generation, a module within the treatment planning software is configured to automatically label upper and lower arch virtual stage models, grouped by virtual treatment plan stage, using a structured file naming convention. These labels are used to assign virtual stage model file names when a virtual treatment plan is exported from the virtual treatment planning software. Pre-treatment (initial) tooth positions are labeled as stage zero (0) virtual stage models, initial planned tooth movements are labeled as stage one (1) virtual stage models, and the last set of virtual stage models are labeled as stage (xx). The last set of virtual stage models in a virtual treatment plan also represent planned orthodontic treatment performance. Pursuant to the present disclosure, the applied file names persist through the export process and ultimately serve as the object labels for an upper or lower dental arch virtual stage model. The standardized naming convention facilitates automated file retrieval functions within the disclosed computer-implemented system.

In general, the virtual treatment planning phase (see, e.g., phase 210 of FIG. 2) ends when a qualified clinician reviews and approves the planned treatment performance as compared to the preferred clinical outcome. Generally, the current processes of determining final planned tooth positions and approving a virtual treatment plan are almost completely reliant upon visual inspection and clinical experience due to inefficiencies, resource requirements, and technique variability associated with systematic implementation of traditional orthodontic performance evaluation methods. A major driver in this phenomenon may be the general absence of commercially available software tools and resources capable of providing objective data points that could assist this clinical decision making process. Accordingly, one embodiment of the present disclosure could address this gap by configuring the outlined computer implemented software modules to automatically obtain virtual stage models from a virtual treatment plan, determine planned treatment scores, then output planned treatment scores to a graphical user interface (GUI) to inform technicians and clinicians in evaluating and approving the final tooth positions of a virtual treatment plan. The measurement module could be configured with instructions for additional measurements, or new measurement modules, machine learning modules, or some combination thereof, and could be configured, attached, and trained to provide individual tooth movement confidence and predictability scores, enhanced case complexity scores, periodontal health scores, and dental health scores. Other possible implementations include configuring measurement modules to group individual tooth movement measurements by anatomical region to determine regional tooth movement complexity scores by stage and predicting movement success for each planned tooth movement across all stages of a virtual treatment plan. These scores, in addition to overall treatment success predictions, would be accessed through a graphical user interface module to guide a virtual treatment plan approval process.

Machine Learning

According to one embodiment of the present disclosure, a non-transitory computer implemented system and method is specifically tailored to facilitate a decentralized treatment plan approval process where a generated virtual treatment plan requires approval by the prescribing clinician prior to manufacturing aligners. Alternatively, this proposed embodiment could also exist as one distinct module within an integrated computer implemented software system comprising multiple evaluation modules configured to operate autonomously and output data values to, or recall data values from, a non-transitory computer readable storage medium. Furthermore, the data values from each module could also be stored and managed through a central database module with a user interface configured to facilitate navigation, organization, comparison, manipulation, and evaluation of the stored data across all modules. Additional configurations could be implemented within the central database module to provide instructions to automatically clean, structure, prepare, and distribute the managed data values in real-time, or near real-time, for use in training, informing, and providing continuous feedback to one or more connected machine learning modules, systems, algorithms, or some combination thereof. The central database module could also be configured to automatically push relevant stored data values to any evaluation module when a new evaluation is triggered for a patient, case, or treatment identifier. The evaluation modules could also be configured to receive and use data values from prior evaluations to modify the present scoring classifications, measurement values, or some combination thereof. To compound the efficacy of the described embodiment, a machine learning module could be configured to apply statistical analysis methods to prior evaluation result data. The machine learning module would then assign classifiers, indicators, modifiers, prediction values, confidence values, or some combination thereof, to the evaluation at-hand. Finally, the machine learning modules could be further configured to output the resulting values to the central database module.

Treatment Phase and Retention Phase

The orthodontic treatment phase (see, e.g., phase 220 of FIG. 2) begins with application of stage (1) aligners and continues through the application of the last stage of aligners prescribed in a virtual treatment plan. The final phase of orthodontic treatment is the retention phase (see, e.g., phase 230 of FIG. 2), in which a retainer is manufactured and applied to an upper and lower dental arch to retain the tooth positions achieved via implementation of a prescribed orthodontic treatment plan. In another embodiment of the present disclosure, additional modules could be configured to automatically evaluate final tooth position retention, in comparison to real treatment performance data, when retention stage dental mesh models are submitted by a practice or patient. The module could also be connected with a remote monitoring software system or application, and configured to determine when a retention scan is due in relation to a defined retention scan cadence; and subsequently send instructions to the remote monitoring system to prompt a user or treatment provider to capture and submit the appropriate retention scans.

Planned vs. Real Treatment Performance (T1-T3)

Pursuant to embodiments of the present disclosure, initial case complexity scores are determined using index classifiers representing the measurement values derived from stage (0) virtual stage models, which are identified as "T1." Planned treatment performance scores are determined using index classifiers representing the measurement values derived from stage (xx) virtual stage models, typically identified as "T2." Any set of upper and lower arch virtual stage models can be selected to evaluate the planned treatment performance of a virtual treatment plan stage. Real treatment performance scores are determined using index classifiers representing the measurement values derived from composite stage models obtained during the treatment phase, retention phase, or some combination thereof. Composite stage models are typically identified as "T3." Composite stage models (see, e.g., FIG. 7) can be generated from a set of dental mesh models (see, e.g., FIG. 6), which define real tooth positions at a stage in the treatment phase. Additionally, any set of upper and lower arch composite stage models can be selected to evaluate the real treatment performance of the measured stage of orthodontic treatment. Planned treatment performance and real treatment performance are typically assessed using virtual stage models and composite stage models which represent the same stage of treatment.

Similar embodiments of the present disclosure could implement additional software modules, or adjust existing modules, with configuration instructions to evaluate T1 models and T2 models without T3 models present. In this scenario, T2 models are virtual stage models or composite stage models. Moreover, it is possible to extend evaluation to an unlimited number of virtual stage models, composite stage models, or some combination thereof, across any number of virtual treatment plan versions and treatment iterations associated with a patient. Any model evaluated subsequent to the T3 model is referred to as T-xx, where (xx) represents the next sequential positive integer value in chronological order of the virtual treatment plan, orthodontic treatment, or some combination thereof.

Virtual Stage Models and Segmented Objects (T1-T2)

Following the example presented above, the virtual stage models, which define a virtual treatment plan, are exported from a virtual treatment planning software in the Wavefront .OBJ file format. Commercially available software can be configured to export virtual stage models in this file format, assuming the treatment plan is generated in the same, or compatible, software. However, the majority of treatment planning software are configured to export virtual stage models in the .STL file format.

Typically, a software module is configured with instructions to merge all named objects comprising a virtual stage file into a single 3D object, representing the whole of an upper or lower dental arch. Furthermore, commercially available treatment planning software export modules are usually configured to reorient virtual stage models to facilitate the subsequent 3D printing process. When a virtual stage file is reoriented, the bite registration data points are not maintained. Consequently, the .STL file outputs do not include critical information that defines the relative relationship between corresponding upper and lower dental arches in three-dimensional space. In addition, exported virtual stage models in the .STL file format cannot be accurately re-segmented into the same 3D objects once they are merged; upper and lower arch stage models also cannot be accurately reoriented to the exact same occlusal relationship. However, it is possible to re-export previously created virtual treatment plans with stage models, in the requisite .OBJ file format and containing the required object segmentation and orientation information, by updating the configuration of a treatment planning software export module to include instructions defining the appropriate file format and data structure.

Composite Stage Models (T3)

Embodiments of the present disclosure additionally outline a processing system and method in which dental mesh models, obtained during orthodontic treatment or retention phases, are overlaid onto the stage zero (0) virtual stage models of the corresponding virtual treatment plan. The processing step further comprises repositioning the objects within the virtual stage models to match the real positions of the geometries within the dental mesh models. The processing step further comprises generating new upper and lower arch composite stage models representing the tooth positions defined by the provided dental mesh model, while maintaining the named objects and file format of the stage zero (0) upper and lower virtual stage models. In some embodiments, the dental mesh model may be generated using an intraoral scanner or by digitizing a physical mold of the patient's teeth. The term "dental mesh model" can also refer to a composite stage model derived from a combination of diagnostic dental mesh models, planned stage virtual stage models, and two-dimensional (2D) images depicting the positions of real tooth positions and anatomy of an upper and lower dental arch.

Indices Overview

According to an embodiment of the present invention, a measurement module within the disclosed system, is configured to automatically perform a series of virtual measurements on the processed virtual stage models, composite stage models, or some combination thereof. Index classifiers are then applied to the resulting measurement values and recorded as scores. In the present disclosure, index classifiers are defined by a published and peer-reviewed dental index. The Discrepancy Index (DI), published by the American Board of Orthodontics (ABO) (see, e.g., FIGS. 8 and 29), can be used to systematically evaluate a range of pre-treatment factors known to impact real orthodontic treatment performance by assigning scores to the measurement values then totaling the scores for an overall pre-treatment case complexity score. Similarly, the ABO also published a comprehensive Cast-Radiograph (CR) evaluation method (see, e.g., FIGS. 8, 30*a* and 30*b*), which defines evaluation methods to measure and classify real treatment performance. The DI and CR systems use different quantitative measuring elements for measuring pre-treatment complexity and treatment performance (see, e.g., FIGS. 8, 29, 30*a* and 30*b*). In another embodiment, the applied index classifiers are defined by the Periodontal Screening and Recording Index (PSR), the Index of Recession (IR), the Palatal Recession Index (PR), or a combination thereof.

Measurement Descriptions—DI

According to embodiments of the present invention, a computer implemented measurement module is configured to automatically perform virtual DI measurements on virtual stage models and composite stage models. DI measurements are automatically applied to all obtained virtual models. However, individual teeth can be excluded from evaluation, by way of an example, by excluding third molars when present.

Figure 9:
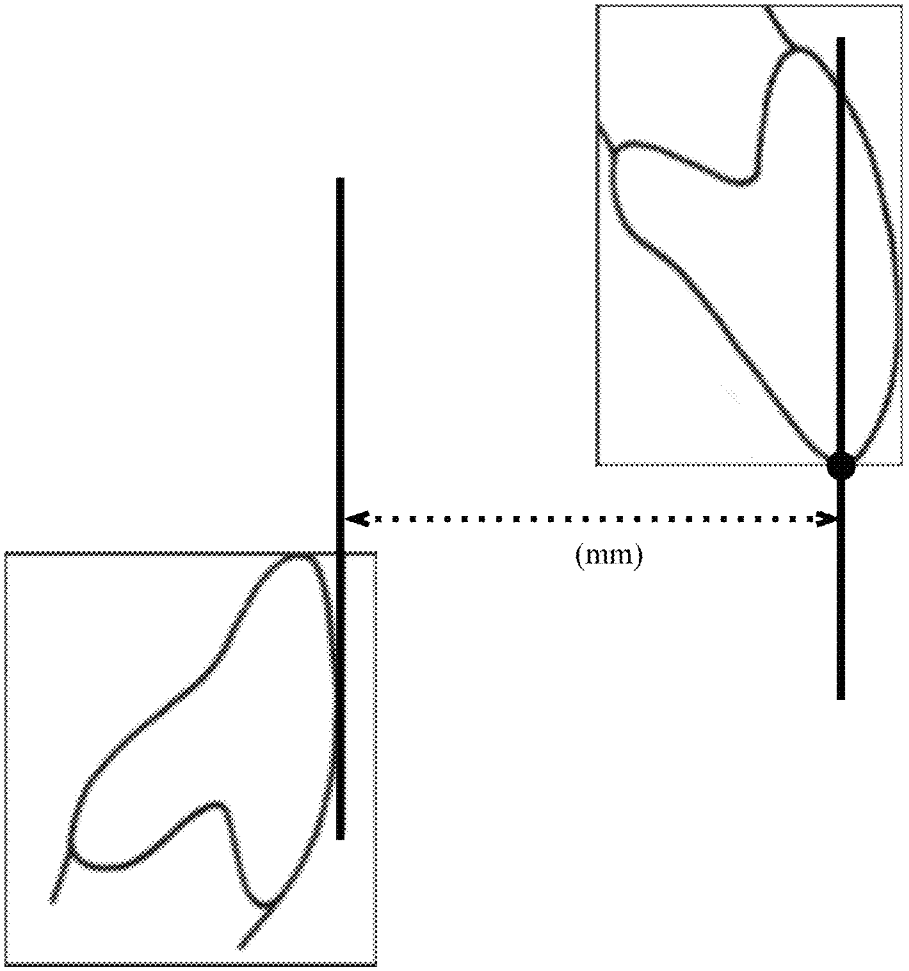
FIG. 9 is an illustration of the first DI measurement, i.e., anterior overjet, according to one embodiment of the invention.

In one embodiment of the present invention, the DI score for “Overjet” is calculated for T1, T2, and/or T3, described above, by way of an example, as a measurement between two antagonistic anterior teeth (lateral or central incisors) comprising the greatest overjet and is measured from the facial surface of the most lingual mandibular tooth to the middle of the incisal edge of the more facially positioned maxillary tooth. For example, FIG. 9 is an illustration of the first DI measurement, i.e., anterior overjet, according to one embodiment of the invention.

Figure 10:
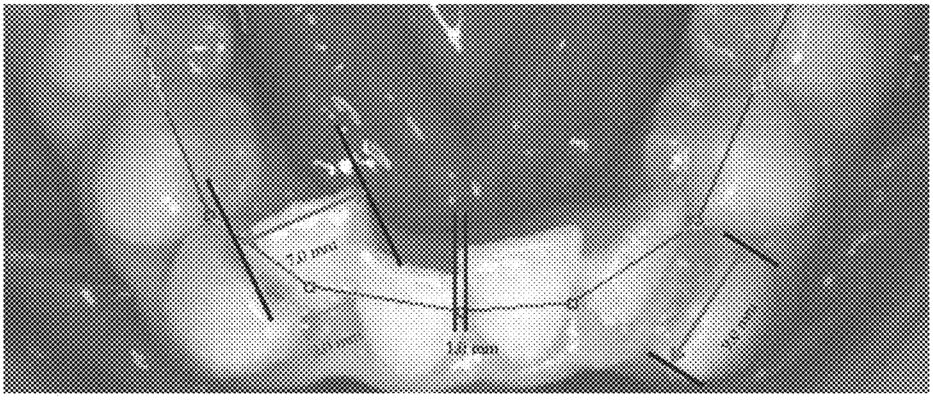
FIG. 10 is an illustration of the second DI measurement, i.e., crowding, according to one embodiment of the invention.

In one embodiment of the present invention, the DI score for “Crowding” is calculated for T1, T2, and/or T3, by way of an example, by measuring, on the arch with the greatest crowding, from the mesial contact point of the right first molar to the mesial contact point of the left first molar. For example, FIG. 10 is an illustration of the second DI measurement, i.e., crowding, according to one embodiment of the invention.

Figure 11:
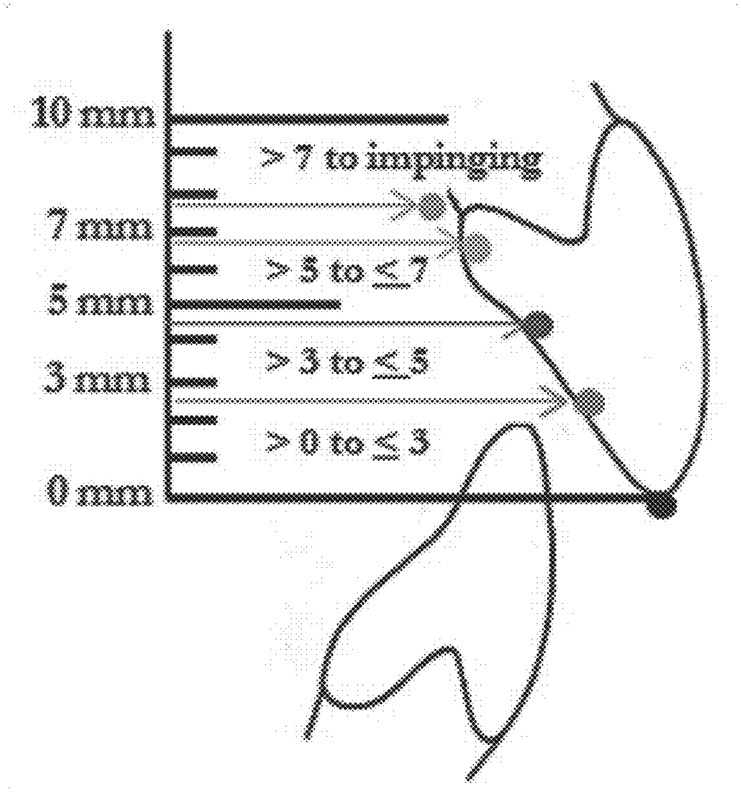
FIG. 11 is an illustration of the third DI measurement, i.e., overbite, according to one embodiment of the invention.

In one embodiment of the present invention, the DI score for “Overbite” is calculated for T1, T2, and/or T3 as, by way of an example, a measurement between two antagonistic anterior teeth (lateral or central incisors) comprising the greatest overbite. For example, FIG. 11 is an illustration of the third DI measurement, i.e., overbite, according to one embodiment of the invention.

Figure 12:
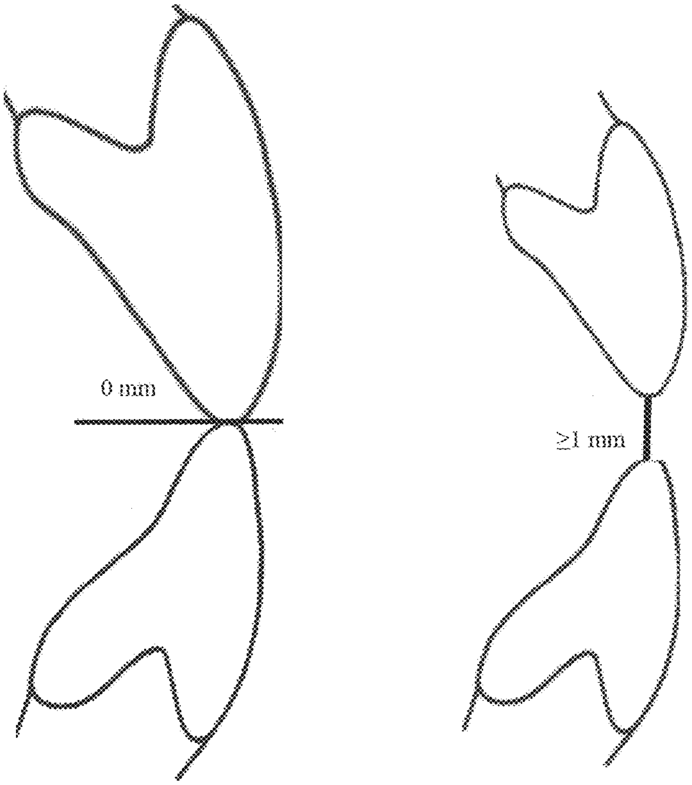
FIG. 12 is an illustration of the fourth DI measurement, i.e., anterior open bite, according to one embodiment of the invention.

In one embodiment of the present invention, the DI score for “Anterior Open Bite” is calculated for T1, T2, and/or T3, by way of an example, by measuring from the incisal edge of the maxillary tooth to the incisal edge of the mandibular tooth for each anterior tooth in an open bite relationship. For example, FIG. 12 is an illustration of the fourth DI measurement, i.e., anterior open bite, according to one embodiment of the invention.

Figure 13:
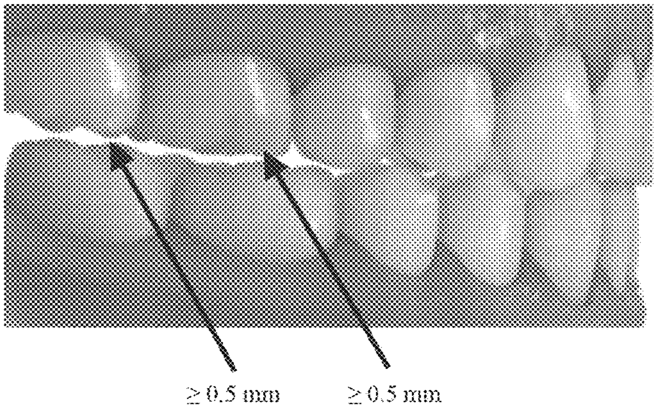
FIG. 13 is an illustration of the fifth DI measurement, i.e., lateral open bite, according to one embodiment of the invention.

In one embodiment of the present invention, the DI score for “Lateral Open Bite” is calculated for T1, T2, and/or T3, by way of an example, by determining each maxillary posterior tooth in an open bite relationship of >0.5 mm from its opposing tooth, with the measurement being from cusp to cusp. For example, FIG. 13 is an illustration of the fifth DI measurement, i.e., lateral open bite, according to one embodiment of the invention.

Figure 14:
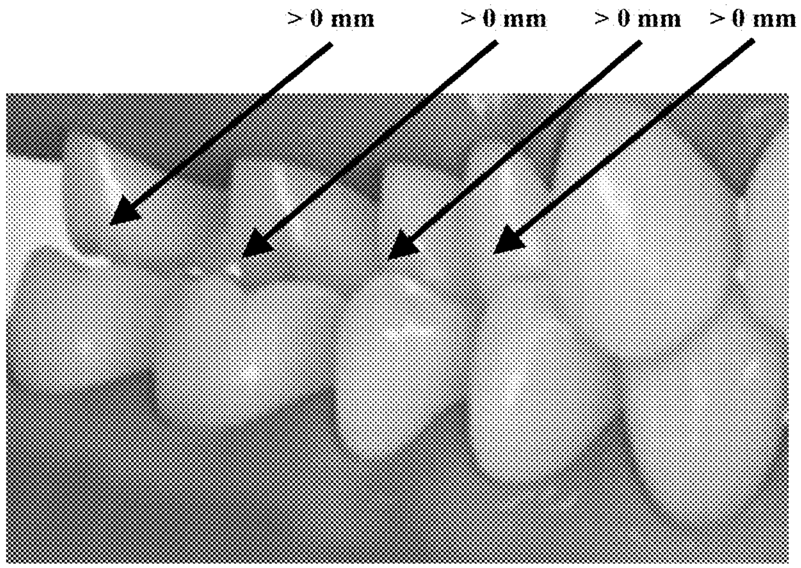
FIG. 14 is an illustration of the sixth DI measurement, i.e., lingual posterior crossbite, according to one embodiment of the invention.

In one embodiment of the present invention, the DI score for “Lingual Posterior Crossbite” is calculated for T1, T2, and/or T3, by way of an example, by identifying each maxillary posterior tooth where the maxillary buccal cusp is >0 mm lingual to the buccal cusp tip of the opposing tooth. For example, FIG. 14 is an illustration of the sixth DI measurement, i.e., lingual posterior crossbite, according to one embodiment of the invention.

Figure 15:
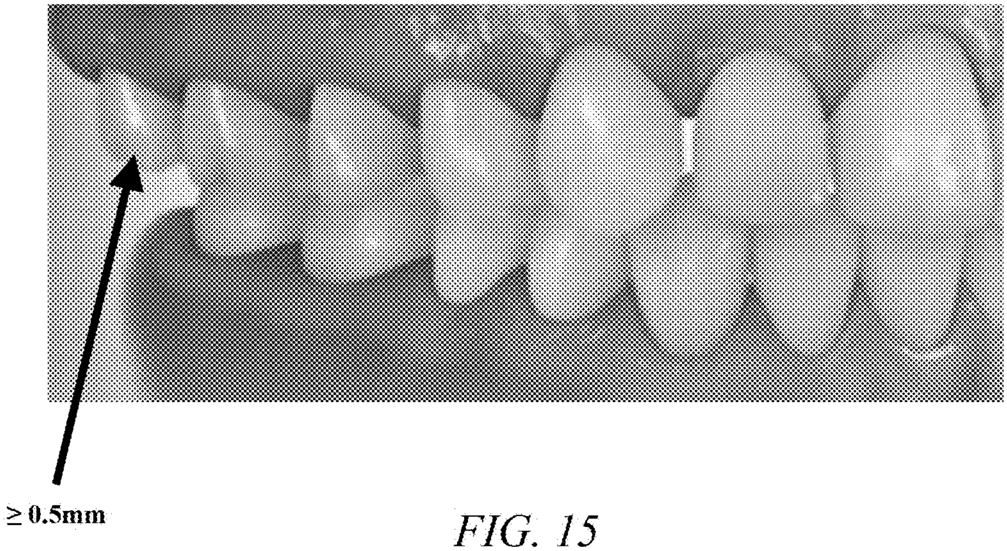
FIG. 15 is an illustration of the seventh DI measurement, i.e., buccal posterior crossbite, according to one embodiment of the invention.

In one embodiment of the present invention, the DI score for “Buccal Posterior Crossbite” is calculated for T1, T2, and/or T3, by way of an example, by identifying each maxillary posterior tooth where the maxillary lingual cusp is >0.5 mm buccal to the buccal cusp of the opposing tooth. For example, FIG. 15 is an illustration of the seventh DI measurement, i.e., buccal posterior crossbite, according to one embodiment of the invention.

Figure 16:
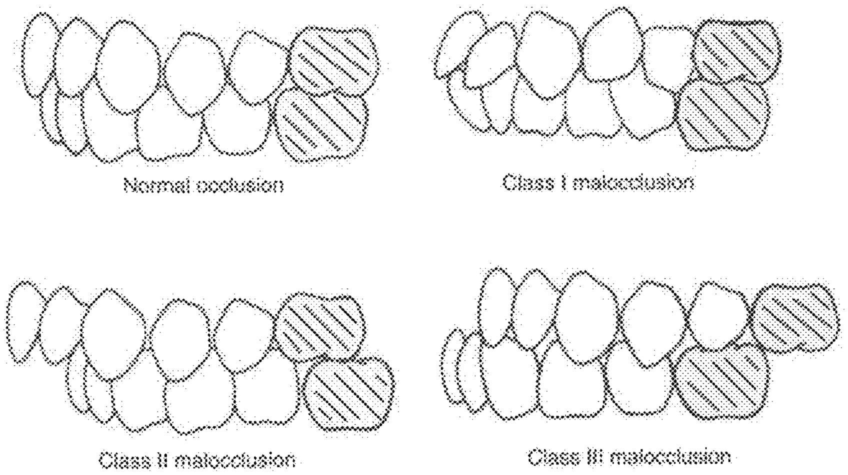
FIG. 16 is an illustration of the eighth DI measurement, i.e., occlusal relationship, according to one embodiment of the invention.

In one embodiment of the present invention, the DI score for “Occlusal Relationship” is calculated for T1, T2, and/or T3, by way of an example, by using the Angle molar classification (i.e., class I, II, or III malocclusion) when arches are in maximum intercuspation. For example, FIG. 16 is an illustration of the eighth DI measurement, i.e., occlusal relationship, according to one embodiment of the invention.

Figure 17:
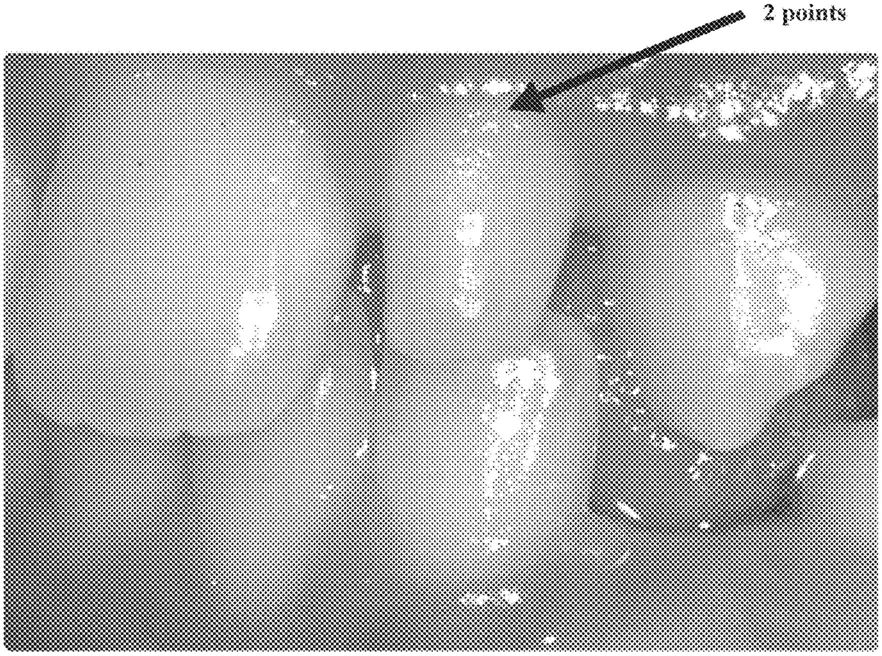
FIG. 17 is an illustration of the ninth DI measurement, i.e., anomalous morphology, according to one embodiment of the invention.

In one embodiment of the present invention, the DI score for “Anomalous Morphology of Tooth Size” is calculated for T1, T2, and/or T3, by way of an example, by comparing the mesial and distal size of each tooth on the right side of the arch with its contralateral tooth. For example, FIG. 17 is an illustration of the ninth DI measurement, i.e., anomalous morphology, according to one embodiment of the invention.

Figure 18A:
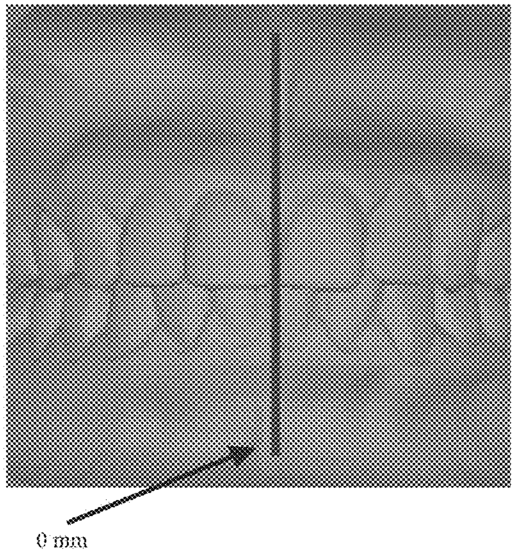
FIGS. 18*a* and 18*b* are illustrations of the tenth DI measurement, i.e., midline discrepancy, according to one embodiment of the invention.
Figure 18B:
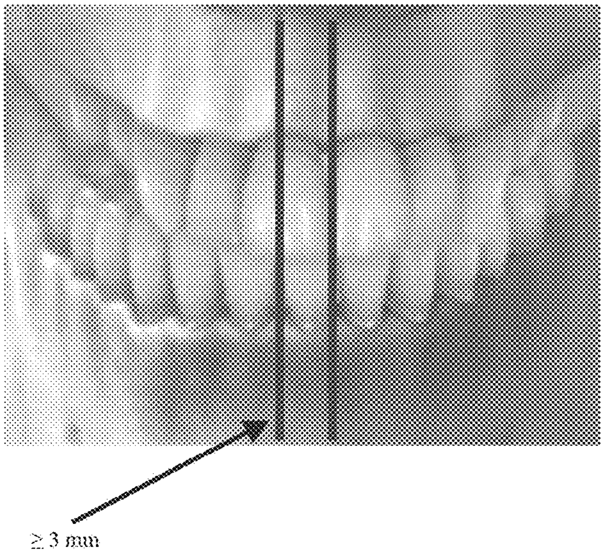

In one embodiment of the present invention, the DI score for “Midline Discrepancy” is calculated for T1, T2, and/or T3, by way of an example, by comparing the difference between a vertical plane representing the anatomical midline for the upper arch and a vertical plane representing the anatomical midline for the lower arch. For example, FIG. 18 is an illustration of the tenth DI measurement, i.e., midline discrepancy, according to one embodiment of the invention.

Figure 19:
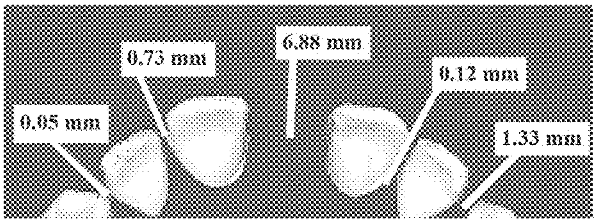
FIG. 19 is an illustration of the eleventh DI measurement, i.e., spacing, according to one embodiment of the invention.

In one embodiment of the present invention, the DI score for “Generalized Spacing” is calculated for T1, T2, and/or T3, by way of an example, by assessing if there is >0.5 mm of space on both sides of any 4 teeth or more. For example, FIG. 19 is an illustration of the eleventh DI measurement, i.e., spacing, according to one embodiment of the invention.

Figure 20:
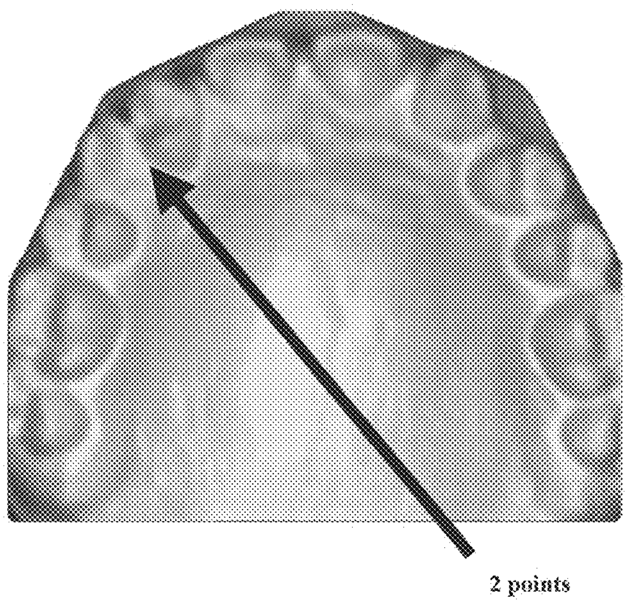
FIG. 20 is an illustration of the twelfth DI measurement, i.e., tooth transposition, according to one embodiment of the invention.

In one embodiment of the present invention, the DI score for “Tooth Transposition” is calculated for T1, T2, and/or T3, by way of an example, when there is an interchange in the position of two permanent adjacent teeth located at the same quadrant in the dental arch. For example, FIG. 20 is an illustration of the twelfth DI measurement, i.e., tooth transposition, according to one embodiment of the invention.

CR Measurements

The present disclosure details a system, according to embodiments of the present invention, which contains a computer implemented measurement module configured to automatically perform virtual CR measurements on virtual stage models and composite stage models. CR measurements are automatically applied to all obtained virtual models. However, individual teeth can be excluded from evaluation, by way of an example, by excluding third molars when present.

Figure 21:
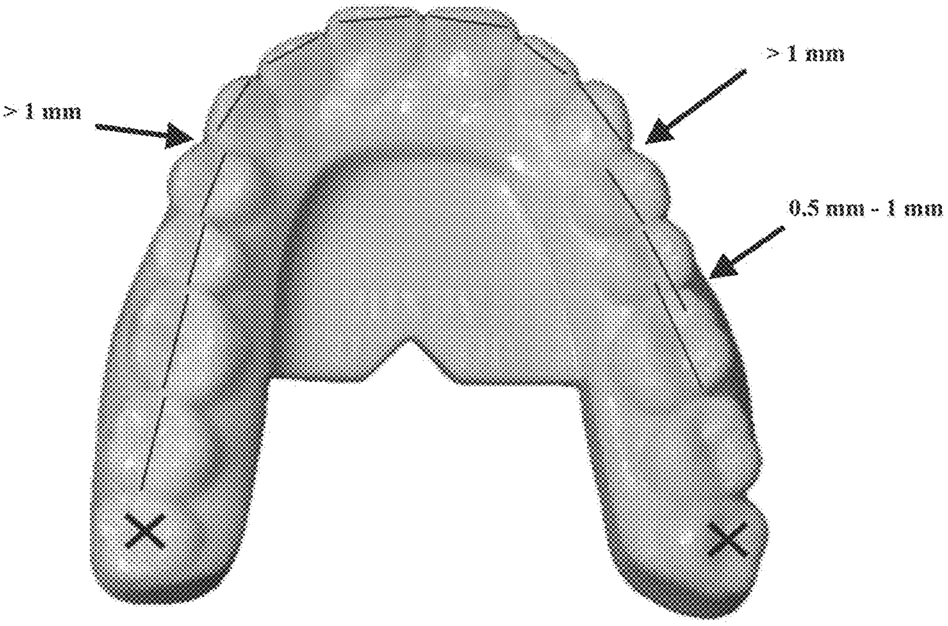
FIG. 21 is an illustration of the first CR measurement, i.e., alignment, according to one embodiment of the invention.

In one embodiment of the present invention, the CR score for “Anterior Alignment” is calculated for T1, T2, and/or T3, by way of an example, based on X axis projections using anatomical landmarks on each anterior tooth’s incisal edge. In one embodiment of the present invention, the CR score for “Posterior Alignment” is calculated for T1, T2, and/or T3, by way of an example, based on the alignment of the central groves of the posterior maxillary teeth, and the mesiobuccal and distobuccal cusps of the mandibular teeth. For example, FIG. 21 is an illustration of the first CR measurement, i.e., alignment, according to one embodiment of the invention.

Figure 22:
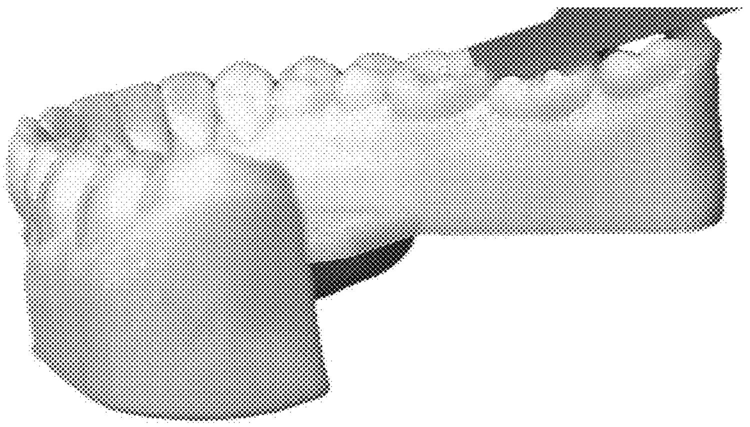
FIG. 22 is an illustration of the second CR measurement, i.e., marginal ridges, according to one embodiment of the invention.

In one embodiment of the present invention, the CR score for “Marginal Ridges” is calculated for T1, T2, and/or T3, by way of an example, by determining and comparing the relative heights of the cementoenamel junction (CEJ) for each tooth. For example, FIG. 22 is an illustration of the second CR measurement, i.e., marginal ridges, according to one embodiment of the invention.

Figure 23:
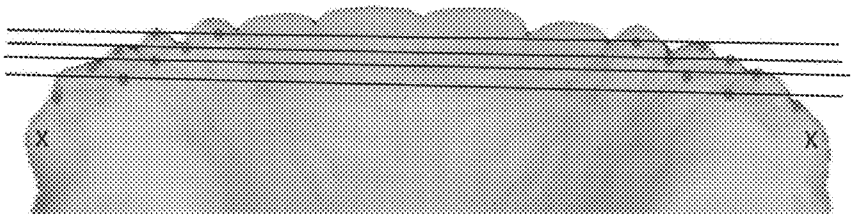
FIG. 23 is an illustration of the third CR measurement, i.e., buccolingual inclination, according to one embodiment of the invention.

In one embodiment of the present invention, the CR score for “Buccolingual Inclination” is calculated for T1, T2, and/or T3, by way of an example, by assessing the difference in height between the buccal and lingual cusps of the maxillary and mandibular molars and premolars using a horizontal plane that is extended between the occlusal surfaces of the right and left posterior teeth. For example, FIG. 23 is an illustration of the third CR measurement, i.e., buccolingual inclination, according to one embodiment of the invention.

Figure 24:
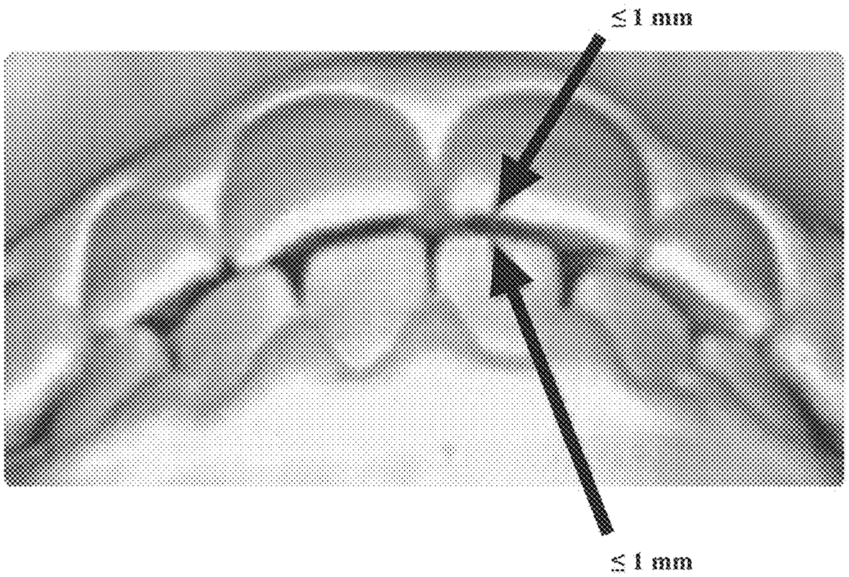
FIG. 24 is an illustration of the fourth CR measurement, i.e., anterior overjet, according to one embodiment of the invention.

In one embodiment of the present invention, the CR score for “Overjet” (post-treatment) is calculated in the anterior for T1, T2, and/or T3, by way of an example, by measuring the deviation of the mandibular canines and incisors from the lingual surfaces of the maxillary canines and incisors. For example, FIG. 24 is an illustration of the fourth CR measurement, i.e., anterior overjet, according to one embodiment of the invention.

Figure 25:
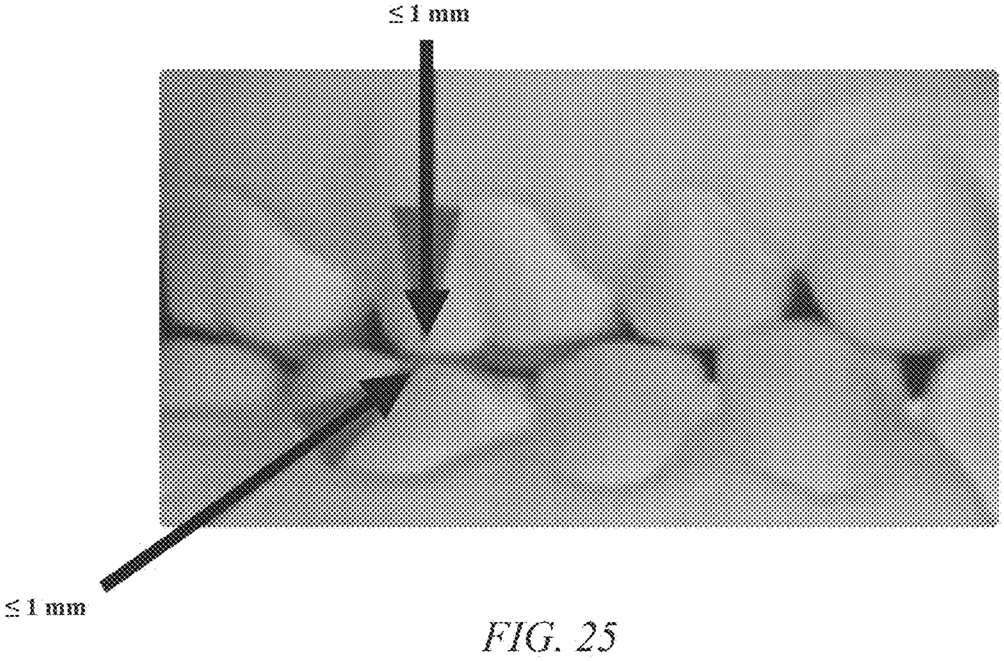
FIG. 25 is an illustration of the fifth CR measurement, i.e., posterior overjet, according to one embodiment of the invention.

In one embodiment of the present invention, the CR score for "Overjet" (post-treatment) is calculated in the posterior for T1, T2, and/or T3, by way of an example, by measuring the deviation of the mandibular buccal cusps from the buccolingual center of the opposing tooth. For example, FIG. 25 is an illustration of the fifth CR measurement, i.e., posterior overjet, according to one embodiment of the invention.

Figure 26:
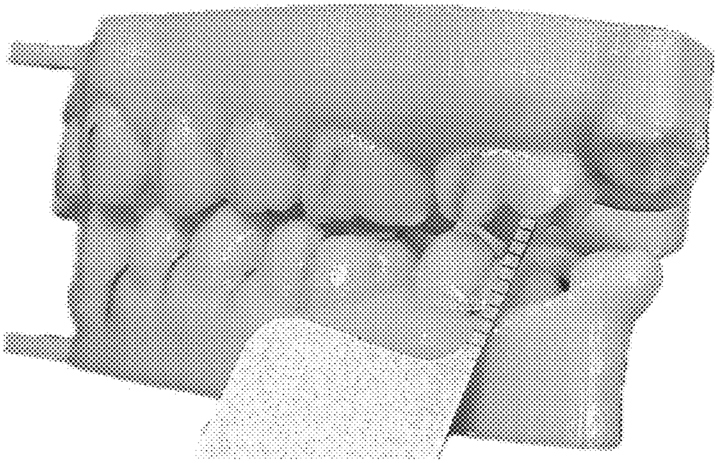
FIG. 26 is an illustration of the sixth CR measurement, i.e., occlusal contacts, according to one embodiment of the invention.

In one embodiment of the present invention, the CR score for "Occlusal Contacts" is calculated for T1, T2, and/or T3, by way of an example, by measuring the occlusal contact of the premolars and molars. Individual teeth may be excluded from this measurement, for example, only functional cusps shall be considered for scoring. For example, FIG. 26 is an illustration of the sixth CR measurement, i.e., occlusal contacts, according to one embodiment of the invention.

Figure 27:
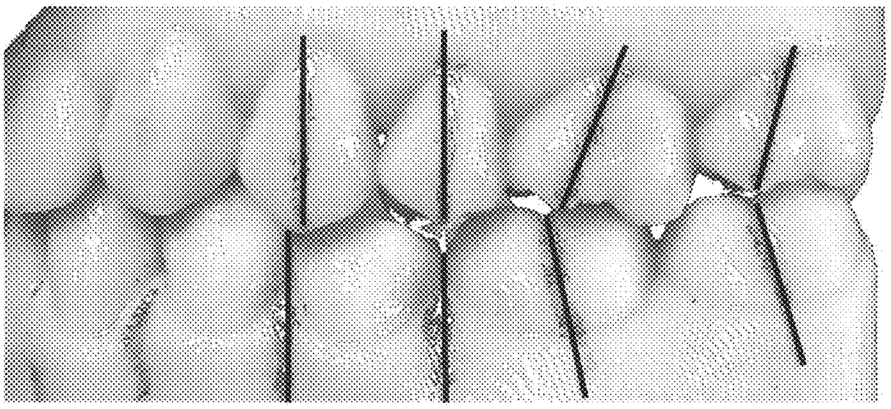
FIG. 27 is an illustration of the seventh CR measurement, i.e., occlusal relationship, according to one embodiment of the invention.

In one embodiment of the present invention, the CR score for "Occlusal Relationship" is calculated for T1, T2, and/or T3, by way of an example, by measuring the alignment of the buccal cusps of the maxillary premolars to the embrasures or contacts between the mandibular premolars and first molar. In another embodiment, the CR score for "Occlusal Relationship" is calculated for T1, T2, and/or T3, by way of an example, by measuring the alignment of the maxillary canine cusp tip to the embrasures or contact between the mandibular canine and adjacent premolar. In another embodiment, the CR score for "Occlusal Relationship" is calculated for T1, T2, and/or T3, by way of an example, by measuring the alignment of the mesiobuccal cusps of the maxillary molars to the buccal grooves of the mandibular molars. For example, FIG. 27 is an illustration of the seventh CR measurement, i.e., occlusal relationship, according to one embodiment of the invention.

Figure 28:
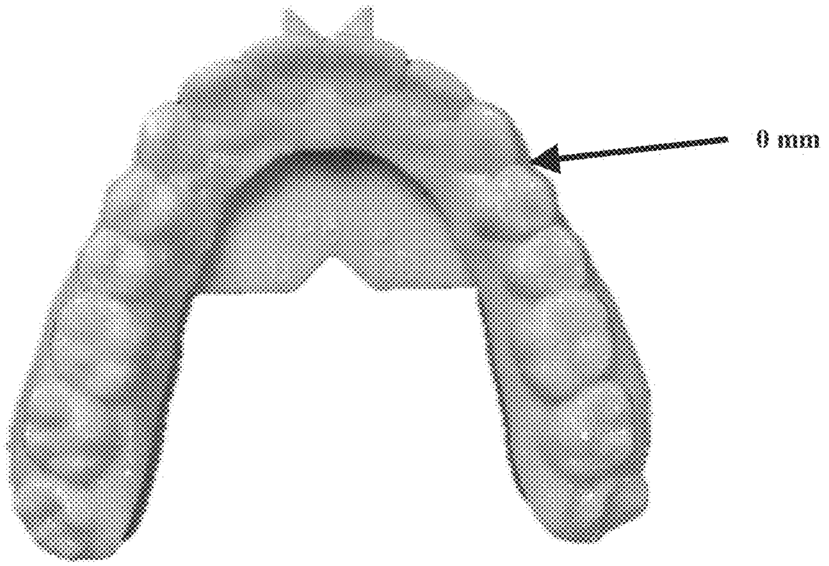
FIG. 28 is an illustration of the eighth CR measurement, i.e., interproximal contact or spaces, according to one embodiment of the invention.

In one embodiment of the present invention, the CR score for "Interproximal Contact or Spaces" is calculated in the posterior for T1, T2, and/or T3, by way of an example, by measuring the contact between the mesial and distal surfaces of each tooth. For example, FIG. 28 is an illustration of the eighth CR measurement, i.e., interproximal contact or spaces, according to one embodiment of the invention.

Gingiva Measurements

In some embodiments of the present invention, virtual measurements are performed on named gingival objects which represent periodontal tissues and positions, otherwise known as soft tissue. The resulting classifications are used to indicate periodontal disease or concerns such as gingival recession.

Total Index Score and Standardized Index Score

After calculating the various DI and CR scores discussed above, the calculated scores (in a file format) are output to the system. For example, FIG. 31 is an illustration of a local output score data file according to one embodiment of the invention. Thereafter, total index scores are calculated from the sum of the individual scores comprising an index (see, e.g., FIG. 33). Additionally, a standardized index score (DI+CR) is generated for pre-treatment (T1) and treatment performance (T3) allowing for direct comparison (apples-to-apples) of pre-treatment case complexity scores and treatment performance scores (see, e.g., FIG. 32). Moreover, the last stage of the virtual treatment plan (T2) is evaluated using the CR elements to compare the virtually planned treatment with the real treatment performance. The last stage from the virtual treatment plan (T2) is also scored using DI elements. The calculated total index scores are combined to generate a standardized index score which allows for direct comparison of planned treatment performance to pre-treatment case complexity and real treatment performance. According to embodiments of the present disclosure, individual scores, total scores, and standardized scores are collectively referred to as "performance scores" or "performance score data."

Central Database

Pursuant to embodiments of the present disclosure, outputting comprises automatically outputting the individual measurement scores (see, e.g., FIG. 33), total index scores (see, e.g., FIG. 33), and standardized index scores (see, e.g., FIG. 32) to a non-transitory computer readable medium accessible through a graphical user interface (GUI), or the central database module (see, e.g., Central Database Module (360) of FIG. 34). The central database module is configured with instructions to process automated and user-selected queries to retrieve, view, manipulate, organize, and report the stored data. The central database module could also be integrated with existing dental practice management systems, allowing for seamless data input and retrieval of patient information.

Computing Device

Figure 35:
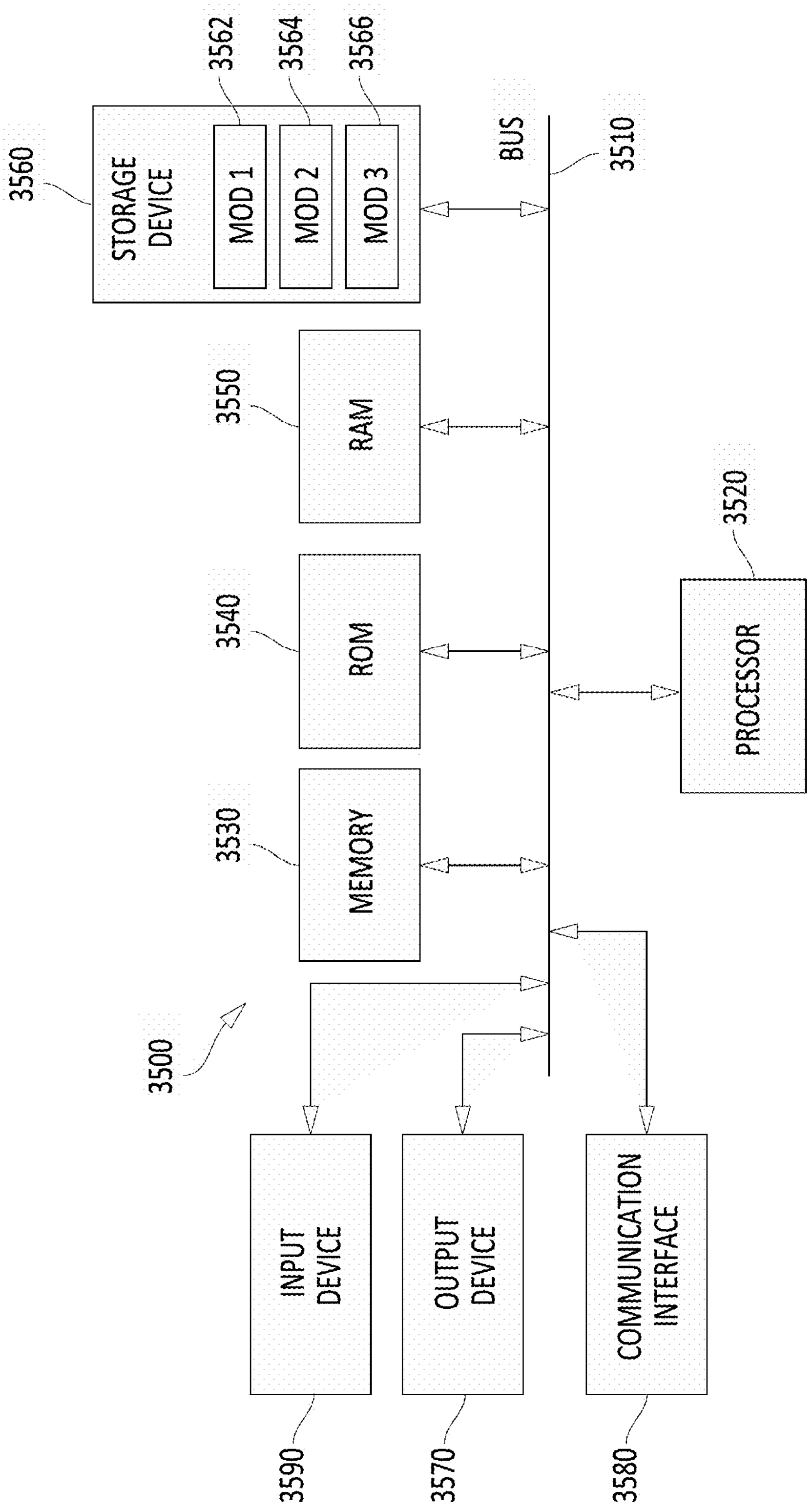
FIG. 35 is a block diagram illustrating a computing device according to some embodiments of the invention.

With reference to FIG. 35, and pursuant to embodiments of the present disclosure, an exemplary system includes a computing device 3500 (such as a general-purpose computing device), including a processing unit (CPU or processor) 3520 and a system bus 3510 that couples various system components including the system memory 3530 such as read-only memory (ROM) 3540 and random access memory (RAM) 3550 to the processor 3520. The computing device 3500 can include a cache of high-speed memory connected directly with, in close proximity to, or integrated as part of the processor 3520. The computing device 3500 copies data from the system memory 3530 and/or the storage device 3560 to the cache for quick access by the processor 3520. In this way, the cache provides a performance boost that avoids processor 3520 delays while waiting for data. These and other modules can control or be configured to control the processor 3520 to perform various actions. Other system memory 3530 may be available for use as well. The system memory 3530 can include multiple different types of memory with different performance characteristics. It can be appreciated that the disclosure may operate on a computing device 3500 with more than one processor 3520 or on a group or cluster of computing devices networked together to provide greater processing capability. The processor 3520 can include any general-purpose processor and a hardware module or software module, such as module 1 3562, module 2 3564, and module 3 3566 stored in storage device 3560, configured to control the processor 3520 as well as a special-purpose processor where software instructions are incorporated into the actual processor design. The processor 3520 may essentially be a completely self-contained computing system, containing multiple cores or processors, a bus, memory controller, cache, etc. A multi-core processor may be symmetric or asymmetric.

The system bus 3510 may be any of several types of bus structures including a memory bus or memory controller, a peripheral bus, and a local bus using any of a variety of bus architectures. A basic input/output (BIOS) stored in memory ROM 3540 or the like, may provide the basic routine that helps to transfer information between elements within the computing device 3500, such as during start-up. The computing device 3500 further includes storage devices 3560 such as a hard disk drive, a magnetic disk drive, an optical disk drive, tape drive or the like. The storage device 3560 can include software modules 3562, 3564, 3566 for controlling the processor 3520. Other hardware or software modules are contemplated. The storage device 3560 is connected to the system bus 3510 by a drive interface. The drives and the associated computer-readable storage media provide nonvolatile storage of computer-readable instructions, data structures, program modules and other data for the computing device 3500. In one aspect, a hardware module that performs a particular function includes the software component stored in a tangible computer-readable storage medium in connection with the necessary hardware components, such as the processor 3520, system bus 3510, output device 3570 (such as a display or speaker), and so forth, to carry out the function. In another aspect, the system can use a processor and computer-readable storage medium to store instructions which, when executed by a processor (e.g., one or more processors), cause the processor to perform a method or other specific actions. The basic components and appropriate variations are contemplated depending on the type of device, such as whether the computing device 3500 is a small, handheld computing device, a desktop computer, or a computer server.

Although the exemplary embodiment described herein employs the storage device 3560 (such as a hard disk), other types of computer-readable media which can store data that are accessible by a computer, such as magnetic cassettes, flash memory cards, digital versatile disks, cartridges, random access memories (RAMs) 3550, and read-only memory (ROM) 3540, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 3500, an input device 3590 represents any number of input mechanisms, such as a microphone for speech, a touch-sensitive screen for gesture or graphical input, keyboard, mouse, motion input, speech and so forth. An output device 3570 can also be one or more of a number of output mechanisms known to those of skill in the art. In some instances, multimodal systems enable a user to provide multiple types of input to communicate with the computing device 3500. The communications interface 3580 generally governs and manages the user input and system output. There is no restriction on operating on any particular hardware arrangement and therefore the basic features here may easily be substituted for improved hardware or firmware arrangements as they are developed.

The technology discussed herein refers to computer-based systems and actions taken by, and information sent to and from, computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Although the invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

The invention claimed is:

1. A method of automatically determining planned orthodontic treatment scores and treatment performance scores using three-dimensional (3D) virtual models, the method comprising the following steps:

obtaining, in a computer-implemented software system, (a) a set of dental mesh models, wherein the set of dental mesh models comprises at least one digital 3D virtual model of upper and lower dental arches of a patient that define initial tooth positions prior to an orthodontic treatment, and (b) at least one set of virtual stage models, wherein the at least one set of virtual stage models comprises multiple segmented anatomical objects, constructed objects, or a combination thereof that define (i) initial tooth positions of the patient prior to an orthodontic treatment and (ii) planned tooth positions of the patient during one or more treatment stages of the orthodontic treatment;

processing, in the computer-implemented software system, the at least one set of virtual stage models and the set of dental mesh models to create one or more composite stage models by overlaying the set of dental mesh models onto the at least one set of virtual stage models, wherein the one or more composite stage models comprise multiple segmented anatomical objects, constructed objects, or a combination thereof of the upper and lower dental arches of the patient that define real tooth positions of the patient during the one or more treatment stages of the orthodontic treatment;

determining, in the computer-implemented software system, virtual measurement values from geometries in (i) the at least one set of virtual stage models and (ii) the one or more composite stage models, by performing a series of automated virtual measurements comprising virtual Discrepancy Index (DI) measurements and virtual Cast-Radiograph (CR) measurements, using the at least one set of virtual stage models and the one or more composite stage models, wherein the series of automated virtual measurements are performed automatically by the computer-implemented software system;

automatically applying, in the computer-implemented software system, index classifiers to the virtual measurement values to generate DI scores and CR scores for each of pre-treatment (T1), planned treatment performance (T2), and real treatment performance (T3);

combining total DI scores with total CR scores to create standardized index scores for each of the pre-treatment (T1), the planned treatment performance (T2), and the real treatment performance (T3) to generate baseline scores, planned treatment performance scores, and real treatment performance scores; and outputting, from the computer-implemented software system, the baseline scores, the planned treatment performance scores, and the real treatment performance scores based on the standardized index scores to evaluate real treatment performance.

2. The method of claim 1, wherein the obtaining step comprises obtaining virtual stage models defining an orthodontic virtual treatment plan from a non-transitory computer readable medium.

3. The method of claim 2, wherein a set of virtual stage models obtained during the obtaining step defines initial positions of anatomical objects, constructed objects, and gingival tissues within the upper and lower dental arches of the patient.

4. The method of claim 2, wherein a set of virtual stage models obtained during the obtaining step defines planned positions of anatomical objects and constructed objects within the upper and lower dental arches of the patient.

5. The method of claim 1, wherein the obtaining step further comprises obtaining the set of dental mesh models of the upper and lower dental arches of the patient from a non-transitory computer readable medium.

6. The method of claim 5, wherein the set of dental mesh models define real positions of anatomical geometries, of the upper and lower dental arches, during any treatment stage.

7. The method of claim 5, wherein the set of dental mesh models define real positions of anatomical geometries, of the upper and lower dental arches, during a retention stage.

8. The method of claim 1, wherein the processing step further comprises repositioning objects within the at least one set of virtual stage models to match real positions of geometries within the set of dental mesh models.

9. The method of claim 1, wherein the virtual measurements are performed on at least one of (i) geometries within anatomical objects representing tooth structures and positions or (ii) geometries defining anatomical objects which represent periodontal tissues and positions.

10. The method of claim 1, wherein the applying step comprises applying index classifiers to individual measurement values, a group of measurement values, or a combination thereof.

11. The method of claim 1, wherein standardized index scores for an initial stage virtual stage model define planned treatment baseline scores and treatment performance baseline scores.

12. The method of claim 1, wherein standardized index scores for a planned stage virtual stage model define the planned treatment performance scores.

13. The method of claim 1, wherein standardized index scores for a composite virtual stage model define the real treatment performance scores.

14. The method of claim 1, wherein the outputting step comprises automatically outputting individual measurement scores, total index scores, and standardized index scores to a non-transitory computer readable medium.

15. The method of claim 1, wherein at least one virtual stage model of the at least one set of virtual stage models obtained during the obtaining step of the upper and lower dental arches of the patient contains segmented objects and metadata defined by a treatment plan.

16. The method of claim 15, wherein the segmented objects are formed by anatomical geometries or constructed geometries.

17. The method of claim 16, wherein the anatomical geometries represent tooth structures and gingival tissues.

18. The method of claim 16, wherein the constructed geometries represent non-anatomical objects.

19. The method of claim 15, wherein the metadata contains information not expressly defined by geometries of the at least one virtual stage model.

20. The method of claim 1, further comprising obtaining a dental mesh model of the upper and lower dental arches of the patient at a treatment stage or a retention stage of the orthodontic treatment.

21. The method of claim 20, wherein the dental mesh model is generated from at least one of a three-dimensional scanner or a physical mold of the patient's teeth.

22. The method of claim 20, wherein the dental mesh model is generated from a composite stage model derived from a combination of diagnostic dental mesh models, planned virtual stage models, and 2D images depicting positions of real anatomical geometries of the upper and lower dental arches of the patient.

23. A computer-implemented software system for automatically determining orthodontic treatment scores using virtual three-dimensional (3D) dental models, the system comprising of the following modules:

an input module configured to obtain and process (a) a set of dental mesh models, wherein the set of dental mesh models comprises at least one digital 3D virtual model of upper and lower dental arches of a patient that define initial tooth positions prior to an orthodontic treatment, and (b) at least one set of virtual stage models, wherein the at least one set of virtual stage models comprises multiple segmented anatomical objects, constructed objects, or a combination thereof that define (i) initial tooth positions of the patient prior to an orthodontic treatment and (ii) planned tooth positions of the patient during one or more treatment stages of the orthodontic treatment;

a processing module configured to generate one or more composite stage models from the at least one set of virtual stage models and the set of dental mesh models by overlaying the set of dental mesh models onto the at least one set of virtual stage models, wherein the one or more composite stage models comprise multiple segmented anatomical objects, constructed objects, or a combination thereof of the upper and lower dental arches of the patient that define real tooth positions of the patient during the one or more treatment stages of the orthodontic treatment;

a measurement module configured to determine virtual measurement values from geometries in (i) the at least one set of virtual stage models and (ii) the one or more composite stage models, by performing a series of automated virtual measurements comprising virtual Discrepancy Index (DI) measurements and virtual Cast-Radiograph (CR) measurements, using the at least one set of virtual stage models and the one or more composite stage models, wherein the series of automated virtual measurements are performed automatically by the computer-implemented software system;

a scoring module configured to (a) automatically apply index classifiers to the virtual measurement values to generate DI scores and CR scores for each of pre-treatment (T1), planned treatment performance (T2), and real treatment performance (T3);

(b) combine total DI scores with total CR scores to create standardized index scores for each of the pre-treatment (T1), the planned treatment performance (T2), and the real treatment performance (T3) to generate baseline scores, planned treatment performance scores, and real treatment performance scores; and an export module configured to output the baseline scores, the planned treatment scores, and the real treatment performance scores based on the standardized index scores to evaluate real treatment performance.

24. The computer-implemented software system of claim 23, wherein the input module is configured to obtain the at least one set of virtual stage models and the set of dental mesh models from a non-transitory computer readable medium via an user interface.

25. The computer-implemented software system of claim 23, wherein the input module is configured to obtain the at least one set of virtual stage models and the set of dental mesh models by automated retrieval instructions within a virtual computing environment.

26. The computer-implemented software system of claim 23, wherein a set of virtual stage models obtained by the input module defines initial positions of anatomical objects, constructed objects, and gingival tissues within the upper and lower dental arches of the patient.

27. The computer-implemented software system of claim 23, wherein a set of virtual stage models obtained by the input module defines planned positions of anatomical objects and constructed objects within the upper and lower dental arches of the patient.

28. The computer-implemented software system of claim 23, wherein the input module is further configured to obtain the set of dental mesh models of the upper and lower dental arches of the patient from a non-transitory computer readable medium.

29. The computer-implemented software system of claim 28, wherein the set of dental mesh models define real positions of anatomical geometries, of the upper and lower dental arches, during any treatment stage.

30. The computer-implemented software system of claim 28, wherein the set of dental mesh models define real positions of anatomical geometries, of the upper and lower dental arches, during a retention stage.

31. The computer-implemented software system of claim 23, wherein the processing module is further configured to reposition objects within the at least one set of virtual stage models to match real positions of geometries within the set of dental mesh models.

32. The computer-implemented software system of claim 23, wherein the virtual measurements are performed on at least one of (i) geometries within anatomical objects representing tooth structures and positions or (ii) geometries defining anatomical objects which represent periodontal tissues and positions.

33. The computer-implemented software system of claim 23, wherein the scoring module is configured to apply index classifiers to individual measurement values, a group of measurement values, or a combination thereof.

34. The computer-implemented software system of claim 23, wherein standardized index scores for an initial stage virtual stage model define planned treatment baseline scores and treatment performance baseline scores.

35. The computer-implemented software system of claim 23, wherein standardized index scores for a planned stage virtual stage model define the planned treatment performance scores.

36. The computer-implemented software system of claim 32, wherein standardized index scores for a composite virtual stage model define the real treatment performance scores.

37. The computer-implemented software system of claim 23, wherein the export module is configured to automatically output measurement scores, total index scores, and standardized index scores to a non-transitory computer readable medium.

* * * * *